United States Patent
Fotsing et al.

(10) Patent No.: US 11,945,813 B2
(45) Date of Patent: Apr. 2, 2024

(54) 5-SUBSTITUTED 4-AMINO-1H-BENZO[C][1,2,6]THIADIAZINE 2,2-DIOXIDES AND FORMULATIONS AND USES THEREOF

(71) Applicant: Firmenich Incorporated, Plainsboro, NJ (US)

(72) Inventors: Joseph R. Fotsing, San Diego, CA (US); Catherine Tachdjian, San Diego, CA (US); Guy Servant, San Diego, CA (US); Brett Weylan Ching, San Diego, CA (US); Timothy Davis, Santee, CA (US)

(73) Assignee: FIRMENICH INCORPORATED, Plainsboro, NJ (US)

( * ) Notice: Subject to any disclaimer, the term of this patent is extended or adjusted under 35 U.S.C. 154(b) by 618 days.

(21) Appl. No.: 17/266,074

(22) PCT Filed: Aug. 6, 2019

(86) PCT No.: PCT/US2019/045325
§ 371 (c)(1),
(2) Date: Feb. 4, 2021

(87) PCT Pub. No.: WO2020/033420
PCT Pub. Date: Feb. 13, 2020

(65) Prior Publication Data
US 2021/0309654 A1    Oct. 7, 2021

Related U.S. Application Data

(60) Provisional application No. 62/715,669, filed on Aug. 7, 2018.

(51) Int. Cl.
| | | |
|---|---|---|
| C07D 417/14 | (2006.01) | |
| A23L 2/56 | (2006.01) | |
| A23L 2/60 | (2006.01) | |
| A23L 27/00 | (2016.01) | |
| A23L 27/20 | (2016.01) | |
| A23L 27/30 | (2016.01) | |
| C07D 417/12 | (2006.01) | |

(52) U.S. Cl.
CPC ............ *C07D 417/14* (2013.01); *A23L 2/56* (2013.01); *A23L 2/60* (2013.01); *A23L 27/2056* (2016.08); *A23L 27/33* (2016.08); *A23L 27/88* (2016.08); *C07D 417/12* (2013.01); *A23V 2002/00* (2013.01)

(58) Field of Classification Search
CPC .................................................. C07D 417/14
See application file for complete search history.

(56) References Cited

U.S. PATENT DOCUMENTS

| | | |
|---|---|---|
| 3,278,532 A | 10/1966 | Houlihan |
| 3,792,036 A | 2/1974 | Pfleiderer |
| 3,843,804 A | 10/1974 | Evers et al. |
| 3,845,770 A | 11/1974 | Theeuwes et al. |
| 3,857,972 A | 12/1974 | Evers et al. |
| 3,916,899 A | 11/1975 | Theeuwes et al. |
| 3,957,783 A | 5/1976 | Hirohashi et al. |
| 3,960,860 A | 6/1976 | Katz et al. |
| 3,966,965 A | 6/1976 | Sellstedt et al. |
| 4,036,837 A | 7/1977 | Sellstedt et al. |
| 4,137,325 A | 1/1979 | Sellstedt et al. |
| 4,146,716 A | 3/1979 | Cox et al. |
| 4,196,207 A | 4/1980 | Webber et al. |
| 4,377,580 A | 3/1983 | Ueda et al. |
| 4,697,392 A | 10/1987 | Siefried |
| 4,765,539 A | 8/1988 | Noakes et al. |
| 4,906,480 A | 3/1990 | Kashket |

(Continued)

FOREIGN PATENT DOCUMENTS

| | | |
|---|---|---|
| DE | 22 58 403 | 6/1973 |
| DE | 2503736 | 8/1976 |
| DE | 1932402 | 9/1980 |
| EP | 0 227 450 | 7/1987 |
| EP | 0 248 554 | 2/1993 |
| EP | 0 530 994 | 3/1993 |
| EP | 0 584 797 | 3/1994 |
| EP | 0 664 128 | 7/1995 |
| EP | 0 887 344 | 12/1998 |
| ES | 0472163 | 3/1979 |
| ES | 8507558 | 12/1985 |
| GB | 812366 | 4/1959 |

(Continued)

OTHER PUBLICATIONS

Arthur et al., 2015, Toxicological evaluation of two flavors with modifying properties: 3-((4-amino2,2-dioxido-1Hbenzo[c][1,2,6]thiadiazin-5-yl)oxy)-2,2-dimethyl-N-propylpropanamide and (S)-1-(3-(((4-amino-2,2-dioxido-1H-benzo[c][1,2,6]thiadiazin-5—yl)oxy)methyl)piperidin-1-yl)-3-methylbutan-1-one, Food and Chemical Toxicology, 76:33-45.

(Continued)

*Primary Examiner* — Nizal S Chandrakumar
(74) *Attorney, Agent, or Firm* — Knobbe, Martens, Olson & Bear, LLP

(57) ABSTRACT

Disclosed herein are 5-Substituted 4-amino-1H-benzo[c][1,2,6]thiadiazine 2,2-dioxide compounds useful as sweet flavor modifiers. Also disclosed herein are ingestible compositions that include one or more of these compounds in combination with a natural or artificial sweetener.

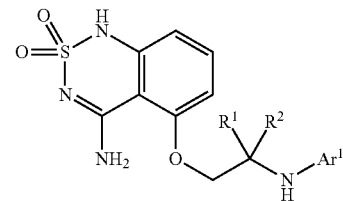

15 Claims, 2 Drawing Sheets

(56) References Cited

U.S. PATENT DOCUMENTS

| | | | |
|---|---|---|---|
| 4,960,870 | A | 10/1990 | Lehmann |
| 5,112,598 | A | 5/1992 | Biesalski |
| 5,192,785 | A | 3/1993 | Lo et al. |
| 5,380,541 | A | 1/1995 | Beyts et al. |
| 5,504,095 | A | 4/1996 | Nakane et al. |
| 5,556,611 | A | 9/1996 | Biesalski |
| 5,698,155 | A | 12/1997 | Grosswald et al. |
| 5,801,180 | A | 9/1998 | Takase et al. |
| 5,950,619 | A | 9/1999 | van der Linden et al. |
| 5,954,047 | A | 9/1999 | Armer et al. |
| 5,970,974 | A | 10/1999 | van der Linden et al. |
| 5,990,117 | A | 11/1999 | Pamukcu et al. |
| 6,013,650 | A | 1/2000 | Thurkauf |
| 6,046,206 | A | 4/2000 | Pamukcu et al. |
| 6,110,920 | A | 8/2000 | Rochus et al. |
| 6,316,454 | B1 | 11/2001 | Uckun et al. |
| 6,316,565 | B1 | 11/2001 | Jung et al. |
| 6,475,544 | B1 | 11/2002 | Hiramoto et al. |
| 6,852,862 | B2 | 2/2005 | Nishizawa et al. |
| 7,105,650 | B2 | 9/2006 | Adler |
| 7,476,399 | B2 | 1/2009 | Tachdjian et al. |
| 7,915,410 | B2 | 3/2011 | Johnson et al. |
| 7,928,111 | B2 | 4/2011 | Tachdjian et al. |
| 8,541,421 | B2 | 9/2013 | Tachdjian et al. |
| 8,586,733 | B2 | 11/2013 | Tachdjian et al. |
| 8,633,186 | B2 | 1/2014 | Tachdjian et al. |
| 8,877,922 | B2 | 11/2014 | Tachdjian et al. |
| 8,968,708 | B2 | 3/2015 | Tachdjian et al. |
| 9,000,054 | B2 | 4/2015 | Tachdjian et al. |
| 9,000,151 | B2 | 4/2015 | Adamski-Werner et al. |
| 9,138,013 | B2 | 9/2015 | Tachdjian et al. |
| 9,181,276 | B2 | 11/2015 | Tachdjian et al. |
| 9,371,317 | B2 | 6/2016 | Adamski-Werner et al. |
| 9,382,196 | B2 | 7/2016 | Tachdjian et al. |
| 9,420,814 | B2 | 8/2016 | Tachdjian et al. |
| 9,475,803 | B2 | 10/2016 | Adamski-Werner et al. |
| 9,603,848 | B2 | 3/2017 | Servant et al. |
| 9,687,015 | B2 | 6/2017 | Tachdjian et al. |
| 9,695,162 | B2 | 7/2017 | Adamski-Werner et al. |
| 9,732,052 | B2 | 8/2017 | Tachdjian et al. |
| 9,745,293 | B2 | 8/2017 | Tachdjian et al. |
| 10,087,154 | B2 | 10/2018 | Tachdjian et al. |
| 10,308,621 | B2 | 6/2019 | Tachdjian et al. |
| 10,570,105 | B2 | 2/2020 | Tachdjian et al. |
| 2002/0025366 | A1 | 2/2002 | Jager et al. |
| 2003/0008344 | A1 | 1/2003 | Adler et al. |
| 2003/0054448 | A1 | 3/2003 | Adler et al. |
| 2003/0232407 | A1 | 12/2003 | Zoller et al. |
| 2004/0127435 | A1 | 7/2004 | Carson et al. |
| 2004/0197453 | A1 | 10/2004 | Hirao et al. |
| 2005/0032158 | A1 | 2/2005 | Adler et al. |
| 2005/0084506 | A1 | 4/2005 | Tachdjian et al. |
| 2005/0196503 | A1 | 9/2005 | Srivastava |
| 2006/0252780 | A1 | 1/2006 | Nakajima |
| 2006/0045953 | A1 | 3/2006 | Tachdjian et al. |
| 2006/0083695 | A1 | 4/2006 | Mori |
| 2006/0134693 | A1 | 6/2006 | Servant et al. |
| 2006/0135552 | A1 | 6/2006 | Malherbe et al. |
| 2006/0257543 | A1 | 11/2006 | Tachdjian et al. |
| 2006/0257550 | A1 | 11/2006 | Mori |
| 2006/0270668 | A1 | 11/2006 | Chew et al. |
| 2007/0003680 | A1 | 1/2007 | Tachdjian et al. |
| 2007/0010402 | A1 | 1/2007 | Ota |
| 2007/0010480 | A1 | 1/2007 | Rusing et al. |
| 2007/0104701 | A1 | 5/2007 | Ueda et al. |
| 2007/0104709 | A1 | 5/2007 | Li et al. |
| 2008/0249189 | A1 | 10/2008 | Atwal |
| 2008/0306053 | A1 | 12/2008 | Tachdjian et al. |
| 2009/0286863 | A1 | 11/2009 | Bruge et al. |
| 2011/0195170 | A1 | 8/2011 | Shigemura et al. |
| 2011/0224155 | A1 | 9/2011 | Tachdjian et al. |
| 2011/0230502 | A1 | 9/2011 | Tachdjian et al. |
| 2011/0245353 | A1 | 10/2011 | Tachdjian et al. |
| 2012/0041078 | A1 | 2/2012 | Tachdjian et al. |
| 2012/0135977 | A1 | 5/2012 | Beshore et al. |
| 2014/0235624 | A1* | 8/2014 | Adamski-Werner .... A61P 27/00 544/11 |
| 2017/0105432 | A1 | 4/2017 | Karanewsky et al. |
| 2017/0119033 | A1 | 5/2017 | Liu et al. |

FOREIGN PATENT DOCUMENTS

| | | | |
|---|---|---|---|
| GB | 951651 | 3/1964 | |
| JP | 59-051290 | 3/1984 | |
| JP | 63-87959 | 4/1988 | |
| JP | 01-197760 | 8/1989 | |
| JP | 02-238856 | 9/1990 | |
| JP | 2001-112433 | 1/2001 | |
| JP | 2003-252875 | 9/2003 | |
| WO | WO 89/00563 | 1/1989 | |
| WO | WO 93/13104 | 7/1993 | |
| WO | WO 98/006722 | 2/1998 | |
| WO | WO 99/59432 | 11/1999 | |
| WO | WO 00/28952 | 5/2000 | |
| WO | WO 00/71524 | 11/2000 | |
| WO | WO 01/04086 | 1/2001 | |
| WO | WO 03/001876 | 1/2003 | |
| WO | WO 03/004992 | 1/2003 | |
| WO | WO 03/007734 | 1/2003 | |
| WO | WO 03/022214 | 3/2003 | |
| WO | WO 03/032944 | 4/2003 | |
| WO | WO 03/051878 | 6/2003 | |
| WO | WO 03/053992 | 7/2003 | |
| WO | WO 03/055866 | 7/2003 | |
| WO | WO 03/076427 | 9/2003 | |
| WO | WO 03/086394 | 10/2003 | |
| WO | WO 04/056365 | 7/2004 | |
| WO | WO 04/087651 | 10/2004 | |
| WO | WO 05/000283 | 1/2005 | |
| WO | WO 05/015158 | 2/2005 | |
| WO | WO 05/016889 | 2/2005 | |
| WO | WO 05/019215 | 3/2005 | |
| WO | WO 05/116069 | 12/2005 | |
| WO | WO 05/123724 | 12/2005 | |
| WO | WO 06/076102 | 7/2006 | |
| WO | WO 06/084184 | 8/2006 | |
| WO | WO 06/113422 | 10/2006 | |
| WO | WO 06/113432 | 10/2006 | |
| WO | WO 07/004709 | 1/2007 | |
| WO | WO 07/047988 | 4/2007 | |
| WO | WO 07/071963 | 6/2007 | |
| WO | WO 08/003378 | 1/2008 | |
| WO | WO 08/024364 | 2/2008 | |
| WO | WO 08/035157 | 3/2008 | |
| WO | WO 08/141333 | 11/2008 | |
| WO | WO 08/147726 | 12/2008 | |
| WO | WO 2010/014666 | * 2/2010 | ........... C07D 285/24 |
| WO | WO 12/001547 | 1/2012 | |
| WO | WO 12/054526 | 4/2012 | |
| WO | WO 13/158928 | 10/2013 | |
| WO | WO 14/023583 | 2/2014 | |
| WO | WO 14/095674 | 6/2014 | |
| WO | WO 14/140864 | 9/2014 | |
| WO | WO 14/025706 | 2/2015 | |

OTHER PUBLICATIONS

Zhou et al., 2008, Novel HCV NS5B polymerase inhibitors derived from 4-(1',1'-dioxo-1',4'-dihydro-1'?6-benzo[1',2',4']thiadiazin-3'-yl)-5-hydroxy-2H-pyridazin-3-ones. Part 2: Variation of the 2- and 6-pyridazin-3-ones. Part 2: variation of the 2- and 6-pyridazinone substituents, Bioorganic & Medicinal Chemistry Letters, 18:1419-1424.

Abdel-Megied et al., 1998, Synthesis of 5,6-dihydronaphtho[1',2':4,5]thieno[2,3-d]pyrimidines, 5,6-dihydronaphtho[1',2':4,5]thieno[3,2-e][1,2,4]triazolo[1,5-c]pyrimidines, and some of their nucleosides, Sulfur Letters, 21(6):269-284.

Abdelrazek et al., 1992, Heterocyclic synthesis with nitriles: synthesis of some novel thiophene and thieno[2,3-d]pyrimidine derivatives, Phosphorus, Sulfur and Silicon and the Related Elements, 72(1-4):93-97.

(56) References Cited

OTHER PUBLICATIONS

Albert et al., 1960, 274. Pteridine Studies. Part XI. The decomposition of 2-hydroxypteridine by alkali, Journal of the Chemical Society, pp. 1370-1373.
Albrecht et al., 1979, Synthesis of 1,2,6-Thiadiazine 1,1-Dioxides via Isoxazolylsulfamides, J. Org. Chem. 44:4191-4194.
Alderman, 1984, A Review of Cellulose Ethers in Hydrophilic Matrices for Oral Controlled-Release Dosage Forms, Int. J. Pharm. Tech. & Prod. Mfr. 5(3):1-9.
Bamba et al., 1979, Release mechanisms in Gelforming Sustained Release Preparations, Int. J. Pharm. 2:307-315.
Bancroft, 1978, Synthesis and Reduction of some 1H-2,1,3-Benzothiadiazin-4(3H)one 2,2-Dioxides, J. Heterocyclic Chem., 15:1521-1523.
Bandurco et al., 1987, Synthesis and cardiotonic activity of a series of substituted 4-alkyl-2(1H)-quinazolinones 1421, J. Med. Chem, 30:1421-1426.
Bassoli et al., 2000, Chapter 3: A rational design of new intensive sweeteners from natural compounds, in Lanzotti et al., eds., Flavour and Fragrance Chemistry, Kluwer Academic Publishers, the Netherlands, pp. 27-36.
Belikov, 1993, Pharmaceutical Chemistry, High School, vol. 1, pp. 43-47.
Bellur et al., 2006, Synthesis of 4-(3-hydroxyalkyl)pyrimidines by ring transformation reactions of 2-alkylidenetetrahydrofurans with amidines, Tetrahedron 62:5426-5434.
Berge et al., 1977, Pharmaceutical Salts, J. Pharm. Sci. 66(1):1-19.
Bhattacharya et al., 1994, Thieno[3',2':4,5][1]benzothieno [2,3-d]pyrimidine derivatives: synthesis and conformation, Journal of the Chemical Society, Perkin Transactions 1: Organic and Bio-Organic Chemistry, 6:689-693.
Blackburn et al., 2006, Identification and characterization of aminopiperidinequinolones and quinazolinones as MCHr1 antagonists, Bioorg. & Med. Chem. Lett. 16:2621-2627.
Blank et al., Pyrimidines. 1970, IX. A New Synthesis of 8-Azapurines and v-Triazolo[4,5-b]pyrimidines, Journal of Organic Chemistry, 35(4):1131-1138.
Blanksma, Oct. 31, 1908, Bereiding der oxymethyl (oxyethyl) cyaannitrobenzolen, Chemisch Weekblad, 5(44):789-795.
Boarland et al., 1951, Monosubstituted Pyrimidines, and the Action of Thiourea on Chloropyrimidines, J. Chem. Soc. 1218-1221.
Brodsky et al., 2005, Oxaziridine-mediated catalytic hydroxylation of unactivated 3° C—H bonds using hydrogen peroxide, J. Am. Chem. Soc., 127:15391-15393, and Supporting Material (16 pp.).
Brown et al., 1956, 66. Pteridine Studies. Part IX. The structure of the monohydroxypteridines and their n-methyl deriviatives, Journal of the Chemical Society, pp. 3443-3453.
Brown, et al., 1990, Evolution of a Series of Peptidoleukotriene Antagonists: Synthesis and Structure-Activity Relationships of 1,6-Disubstituted Indoles and Indazoles, J. Med. Chem. 33:1771-1781.
Buck et al., 1991, A Novel Multigene Family May Encode Odorant Receptors: A Molecular Basis for Odor Recognition, Cell 65(1):175-187.
Calkins, May 2010, 2,1-Benzothiazines: Preparation and Reactivity, PhD thesis, University of Missouri-Columbia, https://mospace.umsystem.edu/xmlui/handle/10355/830; 290 pp.
Campillo et al., 1998, A Novel Tetracyclic System Containing the 1,2,6-Thiadiazine Ring: Synthesis, Structural Assignment and Tautomeric Studies, Heterocycles, 48(3):1833-1840.
Campillo et al., 2004, A study of peculiar tautomerism of pyrido[2,3-c][1,2,6]thiadiazine 2,2-dioxide system, J. Mol. Struct. 678:83-89.
Chandrashekar et al., 2000, T2Rs Function as Bitter Taste Receptors, Cell 100:703-711.
Chemical Abstracts Service, Registry No. 501002-78-4, Entered STN Mar. 31, 2003.
Cheng et al., 1958, Potential Purine Antagonists. XII. Synthesis of 1-Alkyl(aryl)-4,6-disubstituted Pyrazolo [3,4-d] pyrimidines, Journal of Organic Chemistry, 23:852-861.
Cheng et al., 1959, Rearrangment of 4-Amino-6-chloro-1-methylpyrazolo(3,4-d)pyrimidine in Basic Solution, Journal of Organic Chemistry, 24(10):1570-1571.
Chern et al., 1987, A Novel And Efficient Synthesis Of Isoguanosine, Tetrahedron Letters, 28(19):2151-2154.
Chien et al., 2004, Nucleosides XI. Synthesis and Antiviral Evaluation of 5'-Alkylthio-5'-deoxy Quinazolinone Nucleoside Derivatives as S-Adenosyl-L-homocysteine Analogs, Chem. Pharm. Bull. 52(12):1422-1426.
Clauss et al., 1970, Cycloadditionen von Halogensulfonylisocyanaten an Acetylene, Tetrahedron Lett. 2:119-122.
Corbett et al., 2000, Novel 2,2-Dioxide-4,4-disubstituted-1,3-H-2,1,3-benzothiadiazines as Non-Nucleside Reverse Transcriptase Inhibitors, Bioorg. Med. Chem. Lett. 10:193-195.
Da Settimo et al., 2005, Naphtho[1,2-d]isothiazole Acetic Acid Derivatives as a Novel Class of Selective Aldose Reductase Inhibitors, J. Med. Chem. 48:6897-6907.
Dominguez et al., 2000, Efficient synthesis of 4,4-disubstituted-3,4-dihydro-1H-2,1,3-benzothiadiazine 2,2-dioxides, Tetrahedron Lett. 41:9825-9828.
Dorwald, 2005, Side Reactions in Organic Synthesis: A Guide to Successful Synthesis Design, Weinheim: Wiley-VCH Verlag GmbH & Co. KGaA, Preface.
Doucet-Personeni et al., 2001, A Structure-Based Design Approach to the Development of Novel, Reversible AChE Inhibitors, J. Med. Chem., 44:3203-3215.
During et al., 1989, Controlled Release of Dopamine from a Polymeric Brain Implant: In Vivo Characterization, Ann. Neurol. 25:351-356.
El-Gazzar et al., 2002, Studies With Polyfunctionality Substituted Heterocycles: Novel Syntheses Of Thienopyrimido-1,2,4-Triazoles, Phosphorus, Sulfur and Silicon, 177(1):123-136.
Elkholy et al., 2006, Facile synthesis of 5, 6, 7, 8-tetrahydropyrimido [4,5-b]-quinoline derivatives, Molecules, 11(11):890-903.
Elmegeed et al., 2005, Novel synthesizes aminosteroidal heterocycles intervention for inhibiting iron-induced oxidative stress, Eur. J. Med. Chem. 40:1283-1294.
El-Sherbeny et al., 2000, Novel Pyridothienopyrimidine and Pyridothienothiazine Derivatives as Potential Antiviral and Antitumor Agents, Med. Chem. Res. 10:122-135.
Etter et al., 1986, An Enolized Sulfonamide Formed by Strong Hydrogen Bonding to Triphenylphosphine Oxide, J. Org. Chem. 51:5405-5408.
Fan et al., 2004, Transient Silylation of the Guanosine O6 and Amino Groups Facilitates N-Acylation, Organic Letters, 6(15):2555-2557.
Francis et al., 1991, Anxiolytic Properties of Certain Annelated [1,2,4]Triazolo[1,5-c]pyrimidin-5(6H)-ones, J. Med. Chem. 34:2899-2906.
Frauli et al., 2006, Amino-pyrrolidine tricarboxylic acids give new insight into group III metabotropic glutamate receptor activation mechanism, Molecular Pharmacology, 72(3):704-712.
Freidlander, et al., Jan. 12, 1912, Uber brom- und methoxyderivate des indigos, Justus Liebigs Annalen der Chemie, 388:23-49.
Fuentes-Cabrera et al., 2005, Size-expanded DNA bases: an ab initio study of their structural and electronic properties, Journal of Physical Chemistry 8, 109(44):21135-21139.
Garcia-Munoz et al., 1976, Synthesis of Purine-Like Ring Systems Derived From 1,2,6-Thiadiazine 1,1-Dioxide, J. Heterocyclic Chem. 13:793-796.
Ghorab et al., 2006, Novel Antitumor and Radioprotective Sulfonamides Containing Pyrrolo[2,3-d]pyrimidines, Arzneimittel Forschung Drug Research, 56(6):405-413.
Goya et al., 1984, Fused 1,2,6-Thiadiazines: Tetrahydrobenzo[b]thieno[2,3-c] [1,2,6]thiadiazine 2,2-Dioxides, Arch. Pharm. (Weinheim) 317:777-781.
Goya et al., 1985, Fused thiadiazines, Caplus Accession No. 1987:18628, 2 pages, abstract of ES 531159 A1.
Goya et al., 1986, Aminopyrido [2,3-c] [1,2,6] Thiadiazine 2,2-Dioxides: Synthesis and Physico-chemical Properties, Chemica Scripta, 26:607-611.

(56) References Cited

OTHER PUBLICATIONS

Goya et al., 1986, N-Glucosyl-5-Amino-4-Carbamoyl- and 4-Ethoxycarbonylimidazoles as Potential Precursors of 4-Oxoimidazo[4,5-c]-1,2,6-thiadiazine 2,2-Dioxides, Heterocycles 24:3451-3458.
Goya et al., 1987, Synthesis of 2S-Dioxo Isosteres of Purine and Pyrimidine Nucleosides IV. Selective Glycosylation of 4-Amino-5H-Imidazo [4,5-c]-1,2,6-Thiadiazine 2,2-Dioxide, Nucleosides & Nucleotides, 6(3), 631-642.
Goya et al., 1988, Pteridine Analogues; Synthesis and Physico-Chemical Properties of 7-Oxopyrazino [2,3-c][1,2,6] thiadiazine 2,2-Dioxides, Liebigs Ann. Chem., 121-124.
Goya et al., 1988, Synthesis and Cytostatic Screening of an $SO_2$ Analogue of Doridosine, Arch. Pharm. (Weinheim) 321:99-101.
Guedira et al., 1992, Ambident behavior of ketone enolate anions in $S_NAr$ substitutions on fluorobenzonitriel substrates, J. Org. Chem. 57:5577-5585, and Supporting Material.
Harris et al., 1990, Antifolate and Antibacterial Activities of 5-Substituted 2,4-diaminoquinazolines, Journal of Medicinal Chemistry, 33(1):434-444.
Hauser et al., 1953, Synthesis of 5-Phenyl-4,6-Dimethyl-2-Pyrimidol and Derivatives from the Cyclization of Urea with 3-Phenyl-2,4-Pentanedione, J. Org. Chem. 18:588-593.
Hirayama et al., 2002, The Discovery of YM-60828: A Potent, Selective and Orally-Bioavailable Factor Xa Inhibito, Bioorg. & Med. Chem. 10:1509-1523.
Hirohashi et al., 1975, Nuclear magnetic resonance studies of bicyclic thiophene derivatives. I. Ring current effects of the benzene ring on the $H_\alpha$ and $H_\beta$ signals of the thiophene ring in benzoylthiophene, thienopyrimidine, and thienodiazepine derivatives, Bulletin of the Chemical Society of Japan, 48(I):147-156.
Hirota et al., 2003, Synthesis and Biological Evaluation of 2,8-Disubstituted 9-Benzyladenines: Discovery of 8-Mercaptoadenines as Potent Interferon-Inducers, Bioorg. Med. Chem. 11:2715-2722.
Hoon et al., 1991, Putative Mammalian Taste Receptors: A Class of Taste-Specific GPCRs with Distinct Topographic Selectivity. Cell 96:541-551.
Howard et al., 1989, Intracerebral drug delivery in rats with lesion-induced memory deficits, J. Neurosurg. 71:105-112.
Hu et al., 2004, Organic Reactions in Ionic Liquids: Gewald Synthesis of 2-Aminothiophenes Catalyzed by Ethylenediammonium Diacetate, Synthetic Communication 34:3801-3806.
Jordan, 2003, Tamoxifen: A Most Unlikely Pioneering Medicine, Nature Reviews: Drug Discovery 2003, 2:205-213.
Jung et al., 2006, Discovery of Novel and Potent thiazoloquinazolines as Selective Aurora A and B Kinase Inhibitors, J. Med. Chem. 49:955-970.
Justoni et al., Nov.-Dec. 1951, Studi su sostanze a presumibile azione chemioterapica antitubercolare, Il Farmaco, 6:849-858.
Kamal et al., 1988, Cyclization of 2-(Carbamoyloxy)- and 2-(Sulfamoyloxy)benzoates Mediated by Liver Microsomes, J. Org. Chem. 53:4112-4114.
Kamal et al., 1989, Enzymatic Cyclization of 2-(Carbamoyloxy)Benzoates, 2-(Sulfamoyloxy)-Benzoates and 2-(Carbamoyloxy)benzopenones with Yeast and Lipase, Heterocycles 29:1391-1397.
Kanbe et al., 2006, Discovery of thiochroman derivatives bearing a carboxy-containing side chain as orally active pure antiestrogens, Bioorg. & Med. Chem. Lett. 16:4090-4094.
Kanuma et al., 2005, Lead optimization of 4-(dimethylamino)quinazolines, potent and selective antagonists for the melanin-concentrating hormone receptor 1, Bioorg. & Med. Chem. Lett. 15:3853-3856.
Kawai et al., 2002, Taste enhancements between various amino acids and IMP, Chemical Senses 27, 8:739-745.
Khabnadideh et al., 2005, Design, synthesis and evaluation of 2,4-diaminoquinazolines as inhibitors of trypanosomal and leishmanial dihydrofolate reductase, Bioorg. Med. Chem. 13:2637-2649.
Khatoon et al., 2004, Pyrido [2,3-d]pyrimidines and their ribofuranosides: synthesis and antimicrobial evaluations, Indian Journal of Heterocyclic Chemistry, 13(4):331-334.
Klaubert et al., 1981, N-(Aminophenyl)oxamic acids and esters as potent, orally active antiallergy agents, Journal of Medicinal Chemistry, 24(6):742-748.
Klinger et al., 2006, Inhibition of Carbonic Anhydrase-II by Sulfamate and Sulfamide Groups: An Investigation Involving Direct Thermodynamic Binding Measurements, J. Med. Chem. 49:3496-3500 (2006).
Knobloch et al., 1962, Uber die synthese von 2-substituierten imidazo(c)-pyridinen aus 3,4-diaminopyridin, Journal Fuer Praktische Chemie, 4(17):199-212.
Kokrashvili et al., 2009, Taste signaling elements expressed in gut enteroendocrine cells regulate nutrient-responsive secretion of gut hormones, Am. J. Clin Nutr, 90(suppl):1S-4S.
Kyriazis et al., 2012, Sweet taste receptor signaling in beta cells mediates fructose-induced potentation of glucose-stimulated insulin secretion, PNAS Early Edition, 9 pp.
Kyte et al., 1982, A Simple Method for Displaying the Hydropathic Character of a Protein, J. Mol. Biol. 157:105-132.
Langer et al., 1983, Chemical and Physical Structure of Polymers as Carriers for Controlled Release of Bioactive Agents: A Review, J. Macromol. Sci. Rev. Macromol Chem. 23:61-126.
Langer, 1990, New Methods of Drug Delivery, Science 249:1527-1533.
Lee et al., 2006, Acetonitrile-Mediated Synthesis of 2,4-Dichloroquinoline from 2-Ethynyl-aniline and 2,4-Dichloroquinazoline from Anthranilonitrile, Synlett, 2006 No. 1:65-68.
Leistner et al., 1989, Polycyclic azines with heteroatoms in the 1- and 3-positions, Part 22. A facile synthesis of 2-(alkylthio)-4-aminothieno[2,3-d]pyrimidi nes, Archiv. der Pharmazie (Weinheim, Germany), 322(4):227-230.
Levy et al., 1985, Inhibition of Calcification of Bioprosthetic Heart Valves by Local Controlled-Release Diphosphonate, Science 228:190-192.
Li et al., 1997, Preformulation studies for the development of a parenteral liquid formulation of an antitumor agent, AG337, PDA Journal of Pharmaceutical Science and Technology, 51(5):181-186.
Li et al., 2002, Human receptors for sweet and umami taste, Proc. Natl. Acad. Sci. USA 99:4692-4696.
Linkies et al., 1990, Ein neues Verfahren zur Herstellung von 6-Methyl-1,2,3-oxathiazin-4(3H)-on-2,2-dioxid Kaliumsalz (Acesulfam-K), Synthesis 405-406.
Liu et al., 2007, Discovery of a new class of 4-anilinopyrimidines as potent c-Jun N-terminal kinase inhibitors: Synthesis and SAR studies, Bioorg. & Med. Chem. Lett. 17:668-672.
Martinez et al., 2000, Benzothiadiazine Dioxide Dibenzyl Derivatives as Potent Human Cytomegalovirus Inhibitors: Synthesis and Comparative Molecular Field Analysis, J. Med. Chem., 43:3218-3225.
Meyer et al., 1979, Synthesis of fused [1,2,6]thiadiazine 1,1-dioxides as potential transition-state analogue inhibitors of xanthine oxidase and guanase, J. Med. Chem. 22(8):944-948.
Mizushima et al. 1999, Synthesis and properties of N-alkyl amides sulfates, Langmiur, 15:6664-6670.
Naganawa et al., 2006, Further optimization of sulfonamide analogs as EP1 receptor antagonists: Synthesis and evaluation of bioisosteres for the carboxylic acid group, Bioorg. Med. Chem. 14:7121-7137.
Nakashima et al., 1970, The synthesis and structure proof of pyrimido[4-5-d] pyridazines, Journal of Heterocyclic Chemistry, 7:209-210.
Nie et al., 2005, Distinct Contributions of T1R2 and T1R3 Taste Receptor Subunits to the Detection of Sweet Stimuli, Curr. Biol. 15(21):1948-1952.
Norcini et al., 1993, Synthesis and pharmacological evaluation of tyramine congeners containing fused heterocyclic rings, European Journal of Medicinal Chemistry, 28(6):505-511.
Pal et al., 2005, Synthesis and Cyclooxygenase-2 (COX-2) Inhibiting Properties of 1,5-Diarylpyrazoles Possessing N-Substitution on the Sulfonamide ($-SO_2NH_2$) Moiety, Letters in Drug Design & Discovery 2:329-340.
Paronikyan et al., 1993, Synthesis of derivatives of pyrido[2,3-d]pyrimidines condensed with tetrahydropyran and tetrahydrothiopyran, Chemistry of Heterocyclic Compounds, 29(12):1454-1455.

(56) References Cited

OTHER PUBLICATIONS

Paronikyan et al., 1996, synthesis of 2,4-disubstituted pyrimido[4,5-b]indoles, pyrano[4',3':4,5]pyrrolo[2,3-d]pyrimidines and some comversions of pyrimido[4,5-d]indoles, Chemistry of Heterocyclic Compounds, 32(10):1216-1219.

Patil, 1980, The synthesis of thieno[2,3-d]pyrimidine nucleosides related to the naturally occurring nucleosides cytidine and uridine, Journal of the Chemical Society, Perkin Transactions 1: Organic and Bio-Organic Chemistry, 9:1853-1858.

Petersen et al., 1996, Synthesis of heterocycles containing two cytosine or two guanine base-pairing sites: novel tectons for self-assembly, Biorganic & Medicinal Chemistry 4(7):1107-1112.

Poulsen et al., 2001, High-Pressure Synthesis of Enantiomerically Pure C-6 Substituted Pyrazolo[3,4-d]pyrimidines, Bioorganic & Medicinal Chemistry Letters, 11(2):191-193.

PubChemCompound, datasheets, retrieved from internet: cm Nos. 12715714 (Feb. 8, 2007), 12715732 (Feb. 8, 2007); 12715736 (Feb. 8, 2007); 13320183 (Feb. 8, 2007); 19818639 (12-05- 2007); 19851977 (Dec. 5, 2007): 22136223 (Dec. 5, 2007): 22664816 (No longer available online): 24777415-24777421 (May 12, 2008); 24777776-24777778 (May 12, 2008).

Quinn et al., 1991, 4-Amino-1-phenylpyrrazolo[3,4-d]pyrimidin-6(5H)-one, an Isoguanosine Analogue, Australian Journal of Chemistry, 44(7):1001-1005.

Rad-Moghadam et al., 2006, One-pot Three-component Synthesis of 2-Substituted 4-Aminoquinazolines, J. Heterocyclic Chem. 43:913-916.

Raleigh et al., 1999, Pharmacokinetics of Isotretinoin (ISO) in Rats Following Oral Dosing or Aerosol Inhalation, British J. Cancer 80, Suppl. 2:96 Abstract No. P269.

Raslan et al., Dec. 31, 2000, Reactivity of 3-(benzothiazol-2-yl)-3-oxopropanen itrile: a facile synthesis of novel polysubstituted thiophenes, Heteroatom Chemistry, 11(2):94-101.

Rasmussen et al., 1978, The Electrophilic Addition of Chlorosulfonyl Isocyanate to Ketones. A Convenient Synthesis of Oxazines, Oxathiazines, and Uracils, J. Org. Chem. 38:2114-2115.

Reddy et al., 1988, An Efficient Synthesis of 3,4-Dihydro-4-Imino-2(1H)-Quinazolinones, Synthetic Commun. 18:525-530 (1988).

Robinson et al., 2006, Sulfonamide Ligands Attained through Opening of Saccharin Derivatives, Eur. J. Org. Chem. 19:4483-4489.

Rodriguez-Hahn et al., 1984, A Study of the Thorpe-Ziegler Reaction in Very Mild Conditions, Synthetic Commun. 14:967-972.

Rosowsky et al., 1966, Quinazolines. III. Synthesis of 1,3-Diaminobenzo[f]quinazoline and Related Compounds, J. Org. Chem. 31:2607-2613.

Roy et al., 2006, Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity, J. Org. Chem. 71:382-385.

Saudek et al., 1989, A Preliminary Trial of the Programmable Implantable Medication System for Insulin Delivery, N. Engl. J Med. 321:574-579.

Seijas et al., 2000, Microwave enhanced synthesis of 4-aminoquinazolines, Tetrahedron Lett. 41:2215-2217.

Sharma et al., 2006, Synthesis and QSAR studies on 5-[2-(2-methylprop 1-enyl)-1H benzimidazol-lyl]-4,6-diphenyl-pyrimidin-2-(5H)-thione derivatives as antibacterial agents, Eur. J. Med. Chem. 41:833-840.

Silve et al., Nov. 2005, Delineating a $Ca^{2+}$ Binding Pocket within the Venus Flytrap Module of the Human Calcium Sensing Receptor, The Journal of Biological Chemistry, 280:37917-37923.

Smith et al.,2001, March's Advanced Organic Chemistry, pp. 479-480, 506-507, 510-511, 576-577, 862-865,1179-1180 and 1552-1553, $5^{th}$ Edition, John Wiley & Sins, Inc., 2001.

Soldo et al., 2003, (+)-(S)-Alapyridaine—A general taste enhancer?, Chemical Senses, 28(5):371-379.

Spatola, 1983, Peptide Backbone Modifications: a structure-activity analysis of peptides containing amide bond surrogates, In Chemistry and Biochemistry of Amino Acids, Peptides and Proteins, 7:267-357, Marcell Dekker, NY.

Srivastava et al., 1999, Solid Phase Synthesis of Structurally Diverse Pyrimido[4,5-d] Pyrimidines for the Potential Use in Combinatorial Chemistry, Bioorg. Med. Chem. Lett. 9:965-966.

STN CAS Registry of 92932-14-4, referencing ES53119 (1985) and Goya et al. Archiv der Pharmazie (1984) 317(9).

Suami et al., 1998, Molecular mechanisms of sweet taste 8: saccharin, acesulfame-K, cyclamate and their derivatives, Food Chemistry, 63(3):391-396.

Thurmond et al., Feb. 1, 2008, Synthesis and biological Evaluation of Novel 2,4-diaminoquinazoline Derivatives as SMN2 Promoter Activator for the potential Treatment of spinal Muscular Atrophy, Journal of Medicinal Chemistry., 51 (3):449-469.

Tripathi et al., 1987, Reaction of Flavanones with Chlorosulphonyl Isocyanate, Indian J. Chem. Sect. B 26B:1082-1083.

Trivedi et al., 1989, C2, $N^{6-}$ Distributed Adenosines: Synthesis and Structure-Activity Relationships, Journal of Medicinal Chemistry, 32(8):1667-1673.

Tunaley, 1989, Chapter 11. Perceptual Characteristics of Sweeteners, in Progress in Sweeteners, Greby ed., Elsevier Applied Science, London and New York. pp. 291-309.

Uehling et al., 2006, Biarylaniline Phenethanolamines as Potent and Selective $\beta_3$ Adrenergic Receptor Agonists, J. Med. Chem. 49:2758-2771.

Verma et al., 2000, Osmotically Controlled Oral Drug Delivery, Drug Dev. Ind. Pharm. 26:695-708.

Vippagunta et al., 2001, Crystalline solids, Adv. Drug Deliv. Rev. 48:3-26.

Whitelaw et al., 1991, Synthesis and sensory evaluation of ring-substituted dihydrochalcone sweeteners. 2. Analogues of 3'-carboxyhesperetin dihydrochalcone, a high-potency dihydrochalcone sweetener, Journal of Agricultural and Food Chemistry, 39(4):663-667.

Wiet et al., 1993, Fat concentration affects sweetness and sensory profiles of sucrose, sucralose, and aspartame, Journal of Food Science, 58(3):599-602.

Wiet et al., 1997, Does chemical modification of tastants Merely enhance their intrinsic taste qualitifes? Food Chemistry, 58(4):305-311.

Wilson et al., 2007, Synthesis of 5-deazaflavin derivatives and their activation of p53 in cells, Bioorg. & Med. Chem. 15:77-86.

Wilson, 2000, Traceless Solid-Phase Synthesis of 2,4-Diaminoquinazolines, Org. Lett. 3:585-588.

Winkler et al., 2005, Synthesis and microbial transformation of β-amino nitriles, Tetrahedron 61:4249-4260.

Wright, 1964, The Reaction of Sulfamide with α- and β-Diketones. The Preparation of 1,2,5-thiadiazole 1,1-Dioxides and 1,2,6-Thiadiazine 1,1-Dioxides, J. Org. Chem. 29:1905-1909.

Wright, 1965, The Synthesis of 2,1,3-Benzothiadiazine 2,2-Dioxides and 1,2,3-Benzoxathiazine 2,2-Dioxides, Journal of Organic Chemistry 30(11):3960-3962.

Xu et al., 1999, Purine and Pyridine Nucleotides Inhibit a Noninactivating K1 Current and Depolarize Adrenal Cortical Cells through a G Protein-coupled Receptor, Molecular Pharmacology, 55:364-376.

Xu et al., 2006, Oxidative cyclization of N-alkyl-o-methyl-arenesulfonamides to biologically important saccharin derivatives, Tetrahedron 62:7902-7910.

Yamada et al., 2005, Discovery of Novel and Potent Small-MOLECULE inhibitors of NO and Cytokine Production as Antisepsis Agents: Synthesis and Biological Activity of Alkyl 6-(N-Substituted sulfamoyl)cyclohex-1-ene-1-carboxylate, J. Med. Chem. 48:7457-7467.

Yamamoto ed., Dec. 23, 2003, 16.19.3 Product Subclass 3:Pyrido[3,4-d]pyrimidines, in Science of Synthesis, Cat. 2, 16:1225-1233.

Yoshizawa et al., 2002, Efficient solvent-free Thorpe reaction, Green Chem. 4:68-70.

Zhu et al., 2006, The chemical development of CHIR-258, Chimia, 60:584-592.

Zunszain et al., 2005, Search for the pharmacophore in prazosin for Transport-P, Bioorg. & Med. Chem. 13:3681-3689.

(56) References Cited

OTHER PUBLICATIONS

International Search Report and Written Opinion dated Dec. 5, 2019 in application No. PCT/US2019/045325.

* cited by examiner

5-SUBSTITUTED 4-AMINO-1H-BENZO[C][1,2,6]THIADIAZINE 2,2-DIOXIDES AND FORMULATIONS AND USES THEREOF

CROSS-REFERENCE TO RELATED APPLICATIONS

The present application claims the benefit of priority of U.S. Provisional Application No. 62/715,669, filed Aug. 7, 2018, which is hereby incorporated by reference as though set forth herein in its entirety.

TECHNICAL FIELD

In certain aspects, the present disclosure relates generally novel classes of 4-amino-2,2-dioxo-benzo[c][1,2,6]thiadiazine derivatives. In some further aspects, the present disclosure relates to formulations comprising such compounds, such as ingestible compositions or pharmaceutical compositions. In some further aspects, the disclosure provides methods of using (or uses) of such compounds in various food products, beverages, and other ingestible compositions, as well as in methods of treating various conditions related to modulation of the T1R2/T1R3 receptors. In some embodiments, the disclosure provides methods of using the compounds as flavor enhancers of one or more basic taste modalities.

DESCRIPTION OF RELATED ART

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific.

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, such as delayed onset and lingering of sweetness.

It has been reported that an extra-cellular domain, e.g., the Venus flytrap (VFT) domain of a chemosensory receptor, especially one or more interacting sites within the VFT domain, may be a suitable target for compounds or other entities to modulate the chemosensory receptor or its ligands. Certain compounds have been reported to be modulators of the chemosensory receptors in the T1R family or their ligands.

There is a need in the art for new compounds suitable for modifying receptor function associated with chemosensory or chemosensory related sensation or reaction.

SUMMARY

In a first aspect, the disclosure provides compounds of formula (I):

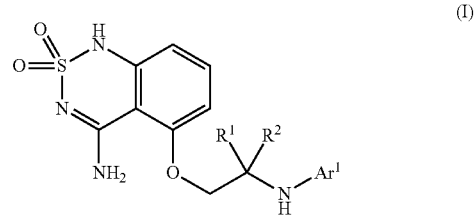

or a salt thereof, wherein:
$R^1$ and $R^2$ are each independently hydrogen or $C_{1-6}$ alkyl, or $R^1$ and $R^2$ together with the carbon to which they are attached is a $C_{3-7}$ carbocyclyl;
$Ar^1$ is an aryl or heteroaryl, each optionally substituted with one or more $R^3$;
each $R^3$ is independently selected from the group consisting of halo, cyano, nitro, oxo, —C(=O)OR$^{3A}$, —NR$^{3A}$(CH$_2$)$_p$OR$^{3B}$, —NR$^{3A}$(CH$_2$)$_p$R$^{3B}$, —(CH$_2$)$_q$OR$^{3B}$, —(CH$_2$)$_q$R$^{3B}$, —C(=O)R$^{3A}$, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, —C(=O)NR$^{3A}$R$^{3B}$, —NR$^{3A}$C(=O)R$^{3B}$, and R$^{3C}$;
each $R^{3A}$ is independently selected from the group consisting of hydrogen, halo, cyano, —(CH$_2$)$_q$R$^{3AA}$, —(CH$_2$)$_q$N(R$^{3AA}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;
each $R^{3B}$ is independently selected from the group consisting of hydrogen, halo, cyano, —(CH$_2$)$_q$R$^{3BB}$, —(CH$_2$)$_q$N(R$^{3BB}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;
each $R^{3C}$ is independently selected from the group consisting of (C$_1$-C$_6$)alkyl, C$_{3-7}$ carbocyclyl, (C$_1$-C$_6$)alkoxy, heterocycle, aryl, heteroaryl, heterocycle(C$_1$-C$_6$)alkyl, aryl(C$_1$-C$_6$)alkyl, heteroaryl(C$_1$-C$_6$)alkyl, and C$_{3-7}$ carbocyclyl, each optionally substituted with one or more $R^{3CC}$;
each $R^{3AA}$ is independently selected from the group consisting of (C$_1$-C$_6$)alkyl, C$_{3-7}$ carbocyclyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more $R^{3CC}$;

each $R^{3BB}$ is independently selected from the group consisting of $(C_1-C_6)$alkyl, $C_{3-7}$ carbocyclyl, $(C_1-C_6)$alkoxy, heterocycle, aryl, heteroaryl, heterocycle$(C_1-C_6)$alkyl, aryl$(C_1-C_6)$alkyl, and $C_{3-7}$ carbocyclyl, each optionally substituted with one or more $R^{3CC}$;

each $R^{3CC}$ is independently selected from the group consisting of halo, cyano, $(C_1-C_6)$alkyl, $C_{3-7}$ carbocyclyl, $(C_1-C_6)$alkoxy, heterocycle, aryl, heteroaryl, heterocycle$(C_1-C_6)$alkyl, aryl$(C_1-C_6)$alkyl, and $C_{3-7}$ carbocyclyl;

each p is independently an integer selected from 1, 2, and 3; and each q is independently an integer selected from 0, 1, 2 and 3.

Further particular embodiments of such compounds are set forth in the Detailed Description, and particularly in the list of embodiments set forth immediately preceding the claims.

In a second aspect, the disclosure provides compositions comprising one or more compounds of the first aspect, according to any embodiments thereof set forth herein. In some embodiments, the compositions are ingestible compositions. In some other embodiments, the compositions are pharmaceutical compositions.

In a third aspect, the disclosure provides methods of using (or uses of) one or more of the compounds of the first aspect, comprising combining one or more compounds of the first aspect with a sweetener, such as a natural or artificial sweetener.

In a fourth aspect, the disclosure provides methods of treating a condition associated with modulation of the T1R2 or the T1R3 receptors, compromising administering one or more compounds of the first aspect to a subject in need thereof.

In a fifth aspect, the disclosure provides compounds of formula (II):

or a salt thereof, wherein:

$Ar^2$ is an aryl or heteroaryl, each optionally substituted with one or more $R^4$;

each $R^4$ is independently selected from the group consisting of halo, cyano, nitro, oxo, $-C(=O)OR^{4A}$, $-NR^{4A}(CH_2)_mOR^{4B}$, $-NR^{3A}(CH_2)_mR^{4B}$, $-(CH_2)_nOR^{4B}$, $-(CH_2)_nR^{4B}$, $-C(=O)R^{4A}$, halo$(C_1-C_6)$alkyl, halo$(C_1-C_6)$alkoxy, $(C_1-C_6)$alkylC$(=O)-$, $(C_1-C_6)$alkylOC$(=O)-$, $(C_1-C_6)$alkylC$(=O)O-$, $-C(=O)NR^{4A}R^{4B}$, $-NR^{4A}C(=O)R^{4B}$, and $R^{4C}$;

each $R^{4A}$ is independently selected from the group consisting of hydrogen, halo, cyano, $-(CH_2)_nOH$, $-(CH_2)_nR^{4AA}$, $-(CH_2)_nOR^{4AA}$, $-(CH_2)_nN(R^{4AA})_2$, $(C_1-C_6)$alkyl, $C_{3-7}$ carbocyclyl, $(C_1-C_6)$alkoxy, halo$(C_1-C_6)$alkyl, halo$(C_1-C_6)$alkoxy, $(C_1-C_6)$alkylC$(=O)-$, $(C_1-C_6)$alkylOC$(=O)-$, $(C_1-C_6)$alkylC$(=O)O-$, heterocycle, aryl, heteroaryl, heterocycle$(C_1-C_6)$alkyl, aryl$(C_1-C_6)$alkyl, and heteroaryl$(C_1-C_6)$alkyl, said heterocycle, aryl and heteroaryl in $R^{4A}$, each optionally substituted with one or more $(C_1-C_6)$alkyl or $C_{3-7}$ carbocyclyl;

each $R^{4B}$ is independently selected from the group consisting of hydrogen, halo, cyano, $-(CH_2)_nOH$, $-(CH_2)_nR^{4BB}$, $-(CH_2)_nOR^{4BB}$, $-(CH_2)_nN(R^{4BB})_2$, $(C_1-C_6)$alkyl, $C_{3-7}$ carbocyclyl, $(C_1-C_6)$alkoxy, halo$(C_1-C_6)$alkyl, halo$(C_1-C_6)$alkoxy, $(C_1-C_6)$alkylC$(=O)-$, $(C_1-C_6)$alkylOC$(=O)-$, $(C_1-C_6)$alkylC$(=O)O-$, heterocycle, aryl, heteroaryl, heterocycle$(C_1-C_6)$alkyl, aryl$(C_1-C_6)$alkyl, and heteroaryl$(C_1-C_6)$alkyl;

each $R^{4C}$ is independently selected from the group consisting of $(C_1-C_6)$alkyl, $C_{3-7}$ carbocyclyl, $(C_1-C_6)$alkoxy, heterocycle, aryl, heteroaryl, heterocycle$(C_1-C_6)$alkyl, aryl$(C_1-C_6)$alkyl, heteroaryl$(C_1-C_6)$alkyl, and $C_{3-7}$ carbocyclyl, each optionally substituted with one or more $R^{4CC}$;

each $R^{4AA}$ is independently selected from the group consisting of hydrogen, $(C_1-C_6)$alkyl, $(C_1-C_6)$alkoxy, heterocycle, aryl, heteroaryl, heterocycle$(C_1-C_6)$alkyl, aryl$(C_1-C_6)$alkyl, and $C_{3-7}$ carbocyclyl, each optionally substituted with one or more $R^{4CC}$;

each $R^{4BB}$ is independently selected from the group consisting of $(C_1-C_6)$alkyl, $(C_1-C_6)$alkoxy, heterocycle, aryl, heteroaryl, heterocycle$(C_1-C_6)$alkyl, aryl$(C_1-C_6)$alkyl, and $C_{3-7}$ carbocyclyl, each optionally substituted with one or more $R^{4CC}$;

each $R^{4CC}$ is independently selected from the group consisting of halo, cyano, $(C_1-C_6)$alkyl, $(C_1-C_6)$alkoxy, heterocycle, aryl, heteroaryl, heterocycle$(C_1-C_6)$alkyl, aryl$(C_1-C_6)$alkyl, and $C_{3-7}$ carbocyclyl;

each m is independently an integer selected from 0, 1, 2, and 3;

each n is independently an integer selected from 0, 1, 2 and 3;

each p is independently an integer selected from 1, 2, and 3; and each q is independently an integer selected from 0, 1, 2 and 3.

Further particular embodiments of such compounds are set forth in the Detailed Description, and particularly in the list of embodiments set forth immediately preceding the claims.

In a sixth aspect, the disclosure provides compositions comprising one or more compounds of the fifth aspect, according to any embodiments thereof set forth herein. In some embodiments, the compositions are ingestible compositions. In some other embodiments, the compositions are pharmaceutical compositions.

In a seventh aspect, the disclosure provides methods of using (or uses of) one or more of the compounds of the fifth aspect, comprising combining one or more compounds of the fifth aspect with a sweetener, such as a natural or artificial sweetener.

In an eighth aspect, the disclosure provides methods of treating a condition associated with modulation of the T1R2 or the T1R3 receptors, compromising administering one or more compounds of the fifth aspect to a subject in need thereof.

Further aspects, and embodiments thereof, are set forth below in the Detailed Description, the Drawings, the Abstract, and the Claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
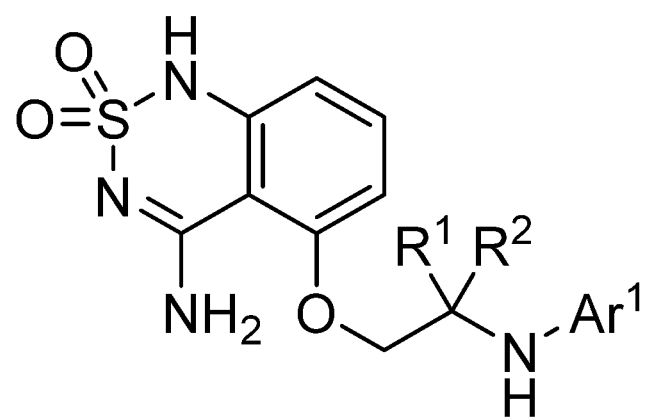
FIG. 1 shows a chemical formula that represents non-limiting examples of novel compounds (or salts thereof) disclosed herein, wherein: $R^1$ and $R^2$ are independently a hydrogen atom or alkyl, or, together with the carbon atom to which they are attached, form a carbocyclic ring; and $Ar^1$ is aryl or heteroaryl, each of which is optionally substituted.
Figure 2:
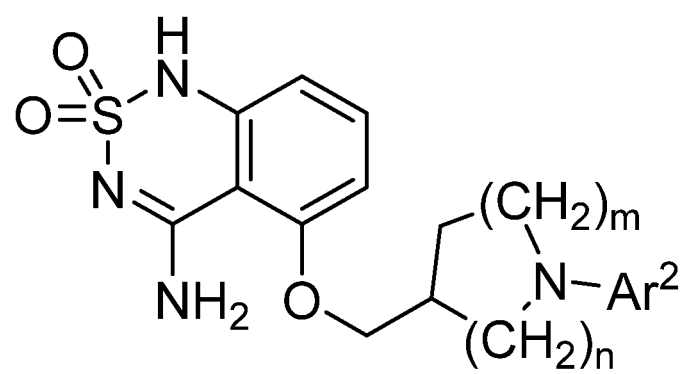
FIG. 2 shows a chemical formula that represents non-limiting examples of novel compounds (or salts thereof) disclosed herein, wherein: n and m are independently 0, 1, 2, or 3; and $Ar^1$ is aryl or heteroaryl, each of which is optionally substituted.

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, "solvate" means a compound formed by the interaction of one or more solvent molecules and one or more compounds described herein. In some embodiments, the solvates are physiologically acceptable solvates, such as hydrates.

As used herein, "$C_a$ to $C_b$" or "$C_{a-b}$" in which "a" and "b" are integers, refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "halogen" or "halo" means any one of the radio-stable atoms of column 7 of the Periodic Table of the Elements, such as fluorine, chlorine, bromine, or iodine. In some embodiments, "halogen" or "halo" refer to fluorine or chlorine.

As used herein, "alkyl" means a straight or branched hydrocarbon chain that is fully saturated (i.e., contains no double or triple bonds). In some embodiments, an alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. Unless indicated to the contrary, the term "alkyl" refers to a group that is not further substituted.

As used herein, "substituted alkyl" means an alkyl group substituted with one or more substituents independently selected from $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

As used herein, "alkoxy" means a moiety of the formula —OR wherein R is an alkyl, as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" means a moiety of the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" means a straight or branched hydrocarbon chain containing one or more double bonds. In some embodiments, the alkenyl group has from 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. Unless indicated to the contrary, the term "alkenyl" refers to a group that is not further substituted.

As used herein, "alkynyl" means a straight or branched hydrocarbon chain containing one or more triple bonds. In some embodiments, the alkynyl group has from 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. Unless indicated to the contrary, the term "alkynyl" refers to a group that is not further substituted.

As used herein, "heteroalkyl" means a straight or branched hydrocarbon chain containing one or more heteroatoms, that is, an element other than carbon, including but not limited to, nitrogen, oxygen, and sulfur, in the chain backbone. In some embodiments, the heteroalkyl group has from 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. Unless indicated to the contrary, the term "heteroalkyl" refers to a group that is not further substituted.

As used herein, "alkylene" means a branched or straight chain fully saturated di-radical chemical group containing only carbon and hydrogen that is attached to the rest of the molecule via two points of attachment (i.e., an alkanediyl). In some embodiments, the alkylene group has from 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene. Unless indicated to the contrary, the term "alkylene" refers to a group that is not further substituted.

As used herein, "alkenylene" means a straight or branched chain di-radical chemical group containing only carbon and hydrogen and containing at least one carbon-carbon double bond that is attached to the rest of the molecule via two points of attachment. In some embodiments, the alkenylene group has from 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl. Unless indicated to the contrary, the term "alkenylene" refers to a group that is not further substituted.

As used herein, "aromatic" means a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" means an aromatic ring or ring system (i.e., two or more fused rings that share two adjacent carbon atoms) containing only carbon in the ring backbone. When the aryl is a ring system, every ring in the system is aromatic. In some embodiments, the aryl group has from 6 to 18 carbon atoms, although the present definition also covers the occurrence of the term "aryl" where no numerical range is designated. In some embodiments, the aryl group has from 6 to 10 carbon atoms. The aryl group may be designated as "$C_{6-10}$ aryl," "$C_6$-$C_{10}$ aryl," or similar designations. Examples of aryl groups include, but are not limited to, phenyl, naphthyl, azulenyl, and anthracenyl. In some embodiments, the term "aryl" refers to phenyl. Unless indicated to the contrary, the term "aryl" refers to a group that is not further substituted As used herein, "aryloxy" and "arylthio" mean moieties of the formulas RO— and RS—, respectively, in which R is an aryl as is defined above, such as "$C_{6-10}$ aryloxy" or "$C_{6-10}$ arylthio" and the like, including but not limited to phenyloxy and phenylthio.

As used herein "aralkyl" or "arylalkyl" means an aryl group connected, as a substituent, via an alkylene group, such as "$C_{7-14}$ aralkyl" and the like, including, but not limited to, benzyl, 2-phenylethyl, 3-phenylpropyl, and the like. In some embodiments, the alkylene group is a lower alkylene group (i.e., a $C_{1-4}$ alkylene group).

As used herein, "heteroaryl" means an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. In some embodiments, the heteroaryl group has from 5 to 18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has from 5 to 10 ring members or from 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl. Unless indicated to the contrary, the term "hereoaryl" refers to a group that is not further substituted.

As used herein, "heteroaralkyl" or "heteroarylalkyl" means heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. In some embodiments, the carbocyclyl group has from 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro [4.4]nonanyl. Unless indicated to the contrary, the term "carbocyclyl" refers to a group that is not further substituted As used herein, "(carbocyclyl)alkyl" means a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system, according to any of the embodiments set forth above for carbocyclyl. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic, and according to any of the embodiments set forth above for carbocyclyl. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. In some embodiments, the heterocyclyl group has from 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "(heterocyclyl)alkyl" means a heterocyclyl group connected, as a substituent, via an alkylene group. Examples include, but are not limited to, imidazolinylmethyl and indolinylethyl.

An "acyl" group refers to a —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—N(R$_A$)C(=O)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—N(R$_A$)C(=S)OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

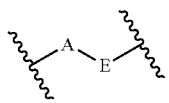

includes the substituent being oriented such that the A is attached at the leftmost attachment point of the molecule as well as the case in which A is attached at the rightmost attachment point of the molecule.

A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "optionally" means that the subsequently described event(s) may or may not occur. In some embodiments, the optional event does not occur. In some other embodiments, the optional event does occur one or more times.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, certain monovalent substituents having only a single atom may be referred to by the name of the atom. For example, in some instances, the substituent "—H" may be referred to as "hydrogen," or the substituent "—F" may be referred to as "fluorine."

Other terms are defined in other portions of this description, even though not included in this subsection.

Compounds that Modulate T1R2/T1R3

In a first aspect, the disclosure provides compounds of formula (I):

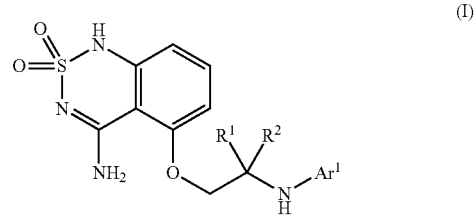

or a salt thereof, wherein:
$R^1$ and $R^2$ are each independently hydrogen or $C_{1-6}$ alkyl, or $R^1$ and $R^2$ together with the carbon to which they are attached is a $C_{3-7}$ carbocyclyl;
$Ar^1$ is an aryl or heteroaryl, each optionally substituted with one or more $R^3$;
each $R^3$ is independently selected from the group consisting of halo, cyano, nitro, oxo, —C(=O)$OR^{3A}$, —$NR^{3A}$($CH_2$)$_p$$OR^{3B}$, —$NR^{3A}$($CH_2$)$_q$$R^{3B}$, —($CH_2$)$_q$$OR^{3B}$, —($CH_2$)$_q$$R^{3B}$, —C(=O)$R^{3A}$, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, —C(=O)$NR^{3A}R^{3B}$, —$NR^{3A}$C(=O)$R^{3B}$, and $R^{3C}$;
each $R^{3A}$ is independently selected from the group consisting of hydrogen, halo, cyano, —($CH_2$)$_q$$R^{3AA}$, —($CH_2$)$_q$N($R^{3AA}$)$_2$, ($C_1$-$C_6$)alkyl, $C_{3-7}$ carbocyclyl, ($C_1$-$C_6$)alkoxy, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, heterocycle, aryl, heteroaryl, heterocycle($C_1$-$C_6$)alkyl, aryl($C_1$-$C_6$)alkyl, and heteroaryl($C_1$-$C_6$)alkyl;
each $R^{3B}$ is independently selected from the group consisting of hydrogen, halo, cyano, —($CH_2$)$_q$$R^{3BB}$, —($CH_2$)$_q$N($R^{3BB}$)$_2$, ($C_1$-$C_6$)alkyl, $C_{3-7}$ carbocyclyl, ($C_1$-$C_6$)alkoxy, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, heterocycle, aryl, heteroaryl, heterocycle($C_1$-$C_6$)alkyl, aryl($C_1$-$C_6$)alkyl, and heteroaryl($C_1$-$C_6$)alkyl;

each $R^{3C}$ is independently selected from the group consisting of $(C_1-C_6)$alkyl, $C_{3-7}$ carbocyclyl, $(C_1-C_6)$alkoxy, heterocycle, aryl, heteroaryl, heterocycle($C_1$-$C_6$)alkyl, aryl($C_1$-$C_6$)alkyl, heteroaryl($C_1$-$C_6$)alkyl, and $C_{3-7}$ carbocyclyl, each optionally substituted with one or more $R^{3CC}$;

each $R^{3AA}$ is independently selected from the group consisting of $(C_1-C_6)$alkyl, $C_{3-7}$ carbocyclyl, $(C_1-C_6)$alkoxy, heterocycle, aryl, heteroaryl, heterocycle($C_1$-$C_6$)alkyl, aryl($C_1$-$C_6$)alkyl, and $C_{3-7}$ carbocyclyl, each optionally substituted with one or more $R^{3CC}$;

each $R^{3BB}$ is independently selected from the group consisting of $(C_1-C_6)$alkyl, $C_{3-7}$ carbocyclyl, $(C_1-C_6)$alkoxy, heterocycle, aryl, heteroaryl, heterocycle($C_1$-$C_6$)alkyl, aryl($C_1$-$C_6$)alkyl, and $C_{3-7}$ carbocyclyl, each optionally substituted with one or more $R^{3CC}$;

each $R^{3CC}$ is independently selected from the group consisting of halo, cyano, $(C_1-C_6)$alkyl, $C_{3-7}$ carbocyclyl, $(C_1-C_6)$alkoxy, heterocycle, aryl, heteroaryl, heterocycle($C_1$-$C_6$)alkyl, aryl($C_1$-$C_6$)alkyl, and $C_{3-7}$ carbocyclyl;

each p is independently an integer selected from 1, 2, and 3; and each q is independently an integer selected from 0, 1, 2 and 3.

In some embodiments thereof, the compounds are compounds of formula (Ia):

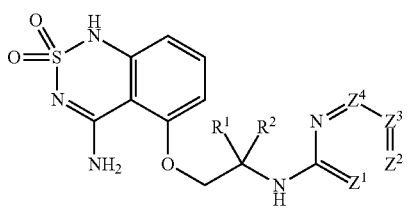

(Ia)

or a salt thereof, wherein $Z^1$ is —CH—, —$CR^3$—, or N (nitrogen);
$Z^2$ is —CH— or —$CR^3$—;
$Z^3$ is —CH—, —$CR^3$—, or N (nitrogen); and
$Z^4$ is —CH— or —$CR^3$—.

In some further such embodiments, $Z^1$ is —CH—. In some other such embodiments, $Z'$ is N (nitrogen). In some such embodiments, $Z^3$ is —CH—. In some other such embodiments, $Z^3$ is N (nitrogen). In some further such embodiments, at least one of $Z^2$ and $Z^4$ is —$CR^3$—.

In some embodiments of any of the foregoing embodiments of the first aspect, each $R^3$ is independently selected from the group consisting of halo, —$NR^{3A}(CH_2)_pOR^{3B}$, —$NR^{3A}(CH_2)_pR^{3B}$, —$(CH_2)_qOR^{3B}$, —$(CH_2)_qR^{3B}$ and $R^{3C}$; each $R^{3A}$ is independently selected from the group consisting of hydrogen, and $(C_1-C_6)$alkyl; each $R^{3B}$ is independently selected from the group consisting of hydrogen, $(C_1-C_6)$alkyl and $C_{3-7}$ carbocyclyl; and each $R^{3C}$ is independently selected from the group consisting of heterocycle and heteroaryl.

The groups $R^1$ and $R^2$ can have any suitable value, as set forth in the embodiments above. In some further embodiments, $R^1$ and $R^2$ are hydrogen. In some other embodiments, $R^1$ and $R^2$ are $C_{1-6}$ alkyl. In some further such embodiments, $R^1$ and $R^2$ are each selected independently from the group consisting of methyl, ethyl, and isopropyl. In some further such embodiments, $R^1$ and $R^2$ are both methyl.

The group $Ar^1$ can have any suitable value, as set forth in the embodiments above. In some embodiments, $Ar^1$ is 2-pyridyl, 2-pyrimidinyl, or 4-pyrimidinyl, each of which is optionally substituted one or more times by substituents independently selected from $R^3$. In some embodiments, $Ar^1$ is 2-pyridyl, 2-pyrimidinyl, or 4-pyrimidinyl, each of which is optionally substituted one or more times by substituents independently selected from the group consisting of $C_{1-6}$ alkyl, —NH—($C_{1-6}$ alkyl), —NH—($C_{1-6}$ alkylene)-OH, —NH—($C_{1-6}$ alkylene)-O—($C_{1-6}$ alkyl), —NH—($C_{1-6}$ alkylene)-($C_{3-10}$ cycloalkyl), pyrrol-1-yl, pyrrolidin-1-yl, pyrazol-1-yl, pyrazolidin-1-yl, imidazole-1-yl, imidazolidin-1-yl, oxazol-1-yl, oxazolidin-1-yl, thiazol-1-yl, thiazolidin-1-yl, piperidin-1-yl, piperazin-1-yl, morpholin-4-yl, and thiomorpoholin-4-yl.

In some embodiments, $Ar^1$ is unsubstituted 2-pyridyl.

In some embodiments, $Ar^1$ is unsubstituted 2-pyrimidinyl. In some other embodiments, $Ar^1$ is 2-pyrimidinyl substituted one or more times by $C_{1-6}$ alkyl, such as methyl.

In some embodiments, $Ar^1$ is unsubstituted 4-pyrimidinyl.

In some other embodiments, $Ar^1$ is 4-pyrimidinyl substituted one or more times by substituents selected from the group consisting of imidazol-1-yl, pyrazol-1-yl, pyrrolidin-1-yl, morpholin-4-yl, and —NH—($C_{1-6}$ alkyl), —NH—($C_{1-6}$ alkylene)-OH, —NH—($C_{1-6}$ alkylene)-O—($C_{1-6}$ alkyl), and —NH—($C_{1-6}$ alkylene)-($C_{3-10}$ cycloalkyl). In some embodiments, $Ar^1$ is 4-pyrimidinyl substituted at the 2-position by $R^3$. In some further embodiments, $Ar^1$ is 4-pyrimidinyl substituted at the 2-position by $C_{1-6}$ alkyl, —NH—($C_{1-6}$ alkyl), —NH—($C_{1-6}$ alkylene)-OH, —NH—($C_{1-6}$ alkylene)-O—($C_{1-6}$ alkyl), —NH—($C_{1-6}$ alkylene)-($C_{3-10}$ cycloalkyl), pyrrol-1-yl, pyrrolidin-1-yl, pyrazol-1-yl, pyrazolidin-1-yl, imidazole-1-yl, imidazolidin-1-yl, oxazol-1-yl, oxazolidin-1-yl, thiazol-1-yl, thiazolidin-1-yl, piperidin-1-yl, piperazin-1-yl, morpholin-4-yl, or thiomorpoholin-4-yl. In some further embodiments, $Ar^1$ is 4-pyrimidinyl substituted at the 2-position by imidazol-1-yl, pyrazol-1-yl, pyrrolidin-1-yl, morpholin-4-yl, —NH—($C_{1-6}$ alkyl), —NH—($C_{1-6}$ alkylene)-OH, —NH—($C_{1-6}$ alkylene)-O—($C_{1-6}$ alkyl), or —NH—($C_{1-6}$ alkylene)-($C_{3-10}$ cycloalkyl).

In some further embodiments, compounds are the compounds identified as 100, 101, 102, 103, 200, 201, 202, 203, 204, 205, 206, 207, or 208, or an ingestibly acceptable salt thereof.

In another aspect, the disclosure provides compounds of formula (II):

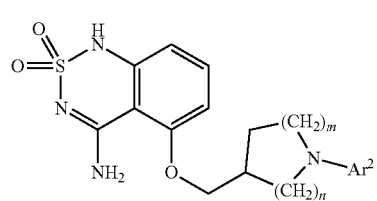

(II)

or a salt thereof, wherein:

$Ar^2$ is an aryl or heteroaryl, each optionally substituted with one or more $R^4$;

each $R^4$ is independently selected from the group consisting of halo, cyano, nitro, oxo, —C(=O)$OR^{4A}$, —$NR^{4A}$($CH_2$)$_m$$OR^{4B}$, —$NR^{3A}$($CH_2$)$_m$$R^{4B}$, —($CH_2$)$_n$$OR^{4B}$, —($CH_2$)$_n$$R^{4B}$, —C(=O)$R^{4A}$, halo($C_1-C_6$)alkyl, halo($C_1-C_6$)alkoxy, ($C_1-C_6$)alkylC(=O)—, ($C_1-C_6$)alkylOC(=O)—, (C$_1$-C$_6$)alkylC(=O)O—, —C(=O)NR$^{4A}$R$^{4B}$, —NR$^{4A}$C(=O)R$^{4B}$, and R$^{4C}$;

each R$^{4A}$ is independently selected from the group consisting of hydrogen, halo, cyano, —(CH$_2$)$_n$OH, —(CH$_2$)$_n$R$^{4AA}$, —(CH$_2$)$_n$OR$^{4AA}$, —(CH$_2$)$_n$N(R$^{4AA}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl, said heterocycle, aryl and heteroaryl in R$^{4A}$, each optionally substituted with one or more (C$_1$-C$_6$)alkyl or C$_{3-7}$ carbocyclyl;

each R$^{4B}$ is independently selected from the group consisting of hydrogen, halo, cyano, —(CH$_2$)$_n$OH, —(CH$_2$)$_n$R$^{4BB}$, —(CH$_2$)$_n$OR$^{4BB}$, —(CH$_2$)$_n$N(R$^{4BB}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;

each R$^{4C}$ is independently selected from the group consisting of (C$_1$-C$_6$)alkyl, C$_{3-7}$ carbocyclyl, (C$_1$-C$_6$)alkoxy, heterocycle, aryl, heteroaryl, heterocycle(C$_1$-C$_6$)alkyl, aryl(C$_1$-C$_6$)alkyl, heteroaryl(C$_1$-C$_6$)alkyl, and C$_{3-7}$ carbocyclyl, each optionally substituted with one or more R$^{4CC}$;

each R$^{4AA}$ is independently selected from the group consisting of hydrogen, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{4CC}$;

each R$^{4BB}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{4CC}$;

each R$^{4CC}$ is independently selected from the group consisting of halo, cyano, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl;

each m is independently an integer selected from 0, 1, 2, and 3;

each n is independently an integer selected from 0, 1, 2 and 3;

each p is independently an integer selected from 1, 2, and 3; and each q is independently an integer selected from 0, 1, 2 and 3.

In some embodiments thereof, the compounds are compounds of formula (IIa):

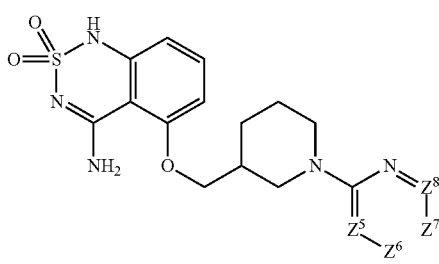

(IIa)

or a salt thereof, wherein $Z^5$ is —CH—, —CR$^4$—, or N (nitrogen);
$Z^6$ is —CH— or —CR$^4$—;
$Z^7$ is —CH—, —CR$^4$—, or N (nitrogen); and
$Z^8$ is —CH— or —CR$^4$—.

In some such embodiments, $Z^5$ is —CH—. In some other such embodiments, $Z^5$ is N (nitrogen). In some such embodiments, at least one of $Z^6$, $Z^7$ and $Z^8$ is —CR$^4$—.

In some further embodiments of any of the foregoing embodiments of this aspect, each R$^4$ is independently selected from the group consisting of halo, —NR$^{4A}$(CH$_2$)$_p$OR$^{4B}$, —NR$^{4A}$(CH$_2$)$_p$R$^{4B}$, —(CH$_2$)$_q$OR$^{4B}$, —(CH$_2$)$_q$R$^{4B}$ and R$^{4C}$; each R$^{4A}$ is independently selected from the group consisting of hydrogen and (C$_1$-C$_6$)alkyl; each R$^{4B}$ is independently selected from the group consisting of hydrogen, (C$_1$-C$_6$)alkyl and C$_{3-7}$ carbocyclyl; and each R$^{4C}$ is independently selected from the group consisting of heterocycle and heteroaryl.

In some further embodiments of any of the foregoing embodiments of this aspect, each R$^4$ is independently selected from the group consisting of —C(=O)OR$^{4A}$, —C(=O)NR$^{4A}$R$^{4B}$, and —C(=O)R$^{4A}$; each R$^{4A}$ is independently selected from the group consisting of hydrogen, —(CH$_2$)$_n$OH, —(CH$_2$)$_n$R$^{4AA}$, —(CH$_2$)$_n$OR$^{4AA}$, —(CH$_2$)$_n$N(R$^{4AA}$)$_2$, aryl, heteroaryl, (C$_1$-C$_6$)alkyl, heterocycle, and heterocycle substituted with one or more (C$_1$-C$_6$)alkyl; each R$^{4B}$ is independently selected from the group consisting of hydrogen, (C$_1$-C$_6$)alkyl, and C$_{3-7}$ carbocyclyl; and each R$^{4C}$ is independently selected from the group consisting of heterocycle and heteroaryl.

In some further embodiments of any of the foregoing embodiments of this aspect, each R$^{4AA}$ is independently selected from the group consisting of hydrogen, (C$_1$-C$_6$)alkyl, C$_{3-7}$ carbocyclyl, heterocycle, aryl and heteroaryl.

The variables m and n can have any suitable values, according to the embodiments set forth above. In some further embodiments, m is 1 or 2. In some further embodiments, m is 2. In some embodiments, n is 1. In some further embodiments, m is 2 and n is 1.

The group Ar$^2$ can have any suitable value, as set forth in the embodiments above. In some embodiments, Ar$^2$ is 2-pyridyl or 2-pyrimidinyl, each of which is optionally substituted one or more times by substituents selected independently from R$^4$. In some embodiments, Ar$^2$ is 2-pyridyl or 2-pyrimidinyl, each of which is optionally substituted one or more times by substituents selected independently from the group consisting of: C$_{1-6}$ alkyl, —C(O)OH, fluorine, C$_{1-6}$ alkoxy, —C(O)—NH—(C$_{1-6}$ alkyl), —C(O)—NH—(C$_{1-6}$ alkylene)-OH, —C(O)—NH—(C$_{1-6}$ alkylene)-O—(C$_{1-6}$ alkyl), —C(O)—NH—(C$_{1-6}$ alkylene)-NH—(C$_{1-6}$ alkyl), —C(O)—NH—(C$_{1-6}$alkylene)-N(C$_{1-6}$alkyl)$_2$, —C(O)—N(C$_{1-6}$alkyl)$_2$, —C(O)—NH—(C$_{3-10}$ cycloalkyl), —C(O)-(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-(C$_{1-6}$ alkyl)-piperazin-1-yl], and —C(O)—NH—(C$_{1-6}$ alkylene)-(C$_{3-10}$ cycloalkyl).

In some embodiments, Ar$^2$ is 2-pyrimidinyl, which is unsubstituted. In some other embodiments, Ar$^2$ is 2-pyrimidinyl, which is substituted once or twice by substituents selected independently from R$^4$. In some further embodiments, Ar$^2$ is 2-pyrimidinyl, which is substituted once or twice by substituents selected independently from the group consisting of: C$_{1-6}$ alkyl, —C(O)OH, fluorine, C$_{1-6}$ alkoxy, —C(O)—NH—(C$_{1-6}$ alkyl), —C(O)—NH—(C$_{1-6}$ alkylene)-OH, —C(O)—NH—(C$_{1-6}$ alkylene)-O—(C$_{1-6}$ alkyl), —C(O)—NH—(C$_{1-6}$ alkylene)-NH—(C$_{1-6}$ alkyl), —C(O)—NH—(C$_{1-6}$ alkylene)-N(C$_{1-6}$ alkyl)$_2$, —C(O)—N(C$_{1-6}$alkyl)$_2$, —C(O)—NH—(C$_{3-10}$ cycloalkyl), —C(O)-

(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-($C_{1-6}$ alkyl)-piperazin-1-yl], and —C(O)—NH—($C_{1-6}$ alkylene)-($C_{3-10}$ cycloalkyl). In some further embodiments, $Ar^2$ is 2-pyrimidinyl, which is substituted once or twice by substituents selected independently from the group consisting of $C_{1-6}$ alkyl, —C(O)OH, fluorine, and $C_{1-6}$ alkoxy. In some further embodiments, $Ar^2$ is 2-pyrimidinyl, which is substituted once or twice by substituents selected independently from the group consisting of methyl, —C(O)OH, fluorine, and methoxy.

In some embodiments, $Ar^2$ is 2-pyridyl, which is unsubstituted. In some other embodiments, $Ar^2$ is 2-pyridyl, which is substituted one or more times by substituents selected independently from $R^4$. In some further embodiments, $Ar^2$ is 2-pyridyl, which is substituted once or twice by substituents selected independently from the group consisting of: $C_{1-6}$ alkyl, —C(O)OH, fluorine, $C_{1-6}$ alkoxy, —C(O)—NH—($C_{1-6}$ alkyl), —C(O)—NH—($C_{1-6}$ alkylene)-OH, —C(O)—NH—($C_{1-6}$ alkylene)-O—($C_{1-6}$ alkyl), —C(O)—NH—($C_{1-6}$ alkylene)-NH—($C_{1-6}$ alkyl), —C(O)—NH—($C_{1-6}$ alkylene)-N($C_{1-6}$ alkyl)$_2$, —C(O)—N($C_{1-6}$ alkyl)$_2$, —C(O)—NH—($C_{3-10}$ cycloalkyl), —C(O)-(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-($C_{1-6}$ alkyl)-piperazin-1-yl], and —C(O)—NH—($C_{1-6}$ alkylene)-($C_{3-10}$ cycloalkyl). In some further embodiments, $Ar^2$ is 2-pyridyl, which is substituted at the 6-position by a substituent selected from $R^4$. In some further embodiments, $Ar^2$ is 2-pyridyl, which is substituted at the 6-position by a substituent selected from the group consisting of: $C_{1-6}$ alkyl, —C(O)OH, fluorine, $C_{1-6}$ alkoxy, —C(O)—NH—($C_{1-6}$ alkyl), —C(O)—NH—($C_{1-6}$ alkylene)-OH, —C(O)—NH—($C_{1-6}$ alkylene)-O—($C_{1-6}$ alkyl), —C(O)—NH—($C_{1-6}$ alkylene)-NH—($C_{1-6}$ alkyl), —C(O)—NH—($C_{1-6}$ alkylene)-N($C_{1-6}$ alkyl)$_2$, —C(O)—N($C_{1-6}$ alkyl)$_2$, —C(O)—NH—($C_{3-10}$ cycloalkyl), —C(O)-(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-($C_{1-6}$ alkyl)-piperazin-1-yl], and —C(O)—NH—($C_{1-6}$ alkylene)-($C_{3-10}$ cycloalkyl). In some further embodiments, $Ar^2$ is 2-pyridyl, which is substituted at the 5-position by a substituent selected from $R^4$. In some further embodiments, $Ar^2$ is 2-pyridyl, which is substituted at the 5-position by a substituent selected from the group consisting of: $C_{1-6}$ alkyl, —C(O)OH, fluorine, $C_{1-6}$ alkoxy, —C(O)—NH—($C_{1-6}$ alkyl), —C(O)—NH—($C_{1-6}$ alkylene)-OH, —C(O)—NH—($C_{1-6}$ alkylene)-O—($C_{1-6}$ alkyl), —C(O)—NH—($C_{1-6}$ alkylene)-NH—($C_{1-6}$ alkyl), —C(O)—NH—($C_{1-6}$ alkylene)-N($C_{1-6}$ alkyl)$_2$, —C(O)—N($C_{1-6}$ alkyl)$_2$, —C(O)—NH—($C_{3-10}$ cycloalkyl), —C(O)-(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-($C_{1-6}$ alkyl)-piperazin-1-yl], and —C(O)—NH—($C_{1-6}$ alkylene)-($C_{3-10}$ cycloalkyl). In some further embodiments, $Ar^2$ is 2-pyridyl, which is substituted at the 4-position by a substituent selected from $R^4$. In some further embodiments, $Ar^2$ is 2-pyridyl, which is substituted at the 4-position by a substituent selected from the group consisting of: $C_{1-6}$ alkyl, —C(O)OH, fluorine, $C_{1-6}$ alkoxy, —C(O)—NH—($C_{1-6}$ alkyl), —C(O)—NH—($C_{1-6}$ alkylene)-OH, —C(O)—NH—($C_{1-6}$ alkylene)-O—($C_{1-6}$ alkyl), —C(O)—NH—($C_{1-6}$ alkylene)-NH—($C_{1-6}$ alkyl), —C(O)—NH—($C_{1-6}$ alkylene)-N($C_{1-6}$ alkyl)$_2$, —C(O)—N($C_{1-6}$ alkyl)$_2$, —C(O)—NH—($C_{3-10}$ cycloalkyl), —C(O)-(pyrrolidin-1-yl), —C(O)-(piperidin-1-yl), —C(O)-(morpholin-4-yl), —C(O)-(thiomorpholin-4-yl), —C(O)-(piperazin-1-yl), —C(O)-[4-($C_{1-6}$ alkyl)-piperazin-1-yl], and —C(O)—NH—($C_{1-6}$ alkylene)-($C_{3-10}$ cycloalkyl).

In some further embodiments, compounds are the compounds identified as 104, 105, 300, 301, 302, 303, 304, 305, 306, 307, 400, 401, 402, 403, 404, 405, 406, 407, 408, 409, 410, 411, 412, 413, 414, 415, 416, 417, 418, 500, 501, 502, 503, 504, 505, 506, 507, 508, 509, 510, 511, 512, 513, 514, 515, 516, 517, 600, 601, 602, 603, 604, 605, 606, 607, 608, 609, 610, 611, 612, 613, 614, 615, 616, 617, 618, or an ingestibly acceptable salt thereof.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine Sweeteners Sweeteners have a wide range of chemically distinct structures and hence possess varying properties, such as, without limitation, odor, flavor, mouthfeel, and aftertaste.

In at least one aspect, the disclosure provides formulations comprising T1R2/T1R3 modulators (of any of the embodiments set forth above, or as any individual compounds of Tables 1-6, or combinations thereof) and one or more sweeteners, such as natural or artificial sweeteners. In some such embodiments, the formulations comprise the one or more sweeteners at concentrations below the concentration of optimal sweetness, if used alone or without the T1R2/T1R3 modulators disclosed herein.

Any suitable natural or artificial sweeteners, or any combinations thereof, may be used. Natural or artificial sweeteners for use in the formulation comprising a sweetener in combination with a flavor enhancer (i.e., the T1R2/T1R3 modulators disclosed herein) include but are not limited to natural or synthetic carbohydrates or carbohydrate analogues, including monosaccharides, disaccharides, oligosaccharides, and polysaccharides, and including rare sugars, or sugars in either of the D- or L-conformations, and include, for example, sucrose, fructose, glucose, L-arabinose, L-fucose, L-glucose, L-ribose, D-arabino-hexulose, psicose, altrose, arabinose, turanose, abequose, allose, abrusoside A, aldotriose, threose, xylose, xylulose, xylo-oligosaccharide (such as xylotriose and xylobiose), lyxose, polydextrose, oligofructose, fucose, galacto-oligosaccharide, galactosamine, galactose, gentio-oligosaccharide (such as gentiobiose, gentiotriose, and gentiotetraose), dextrose, cellobiose, D-leucrose, D-psicose, D-ribose, D-tagatose, trehalose (mycose), neotrehalose, isotrehalose, raffinose, idose, tagatose, melibiose, mannan-oligosaccharide, rhamnose, ribose, ribulose, malto-oligosaccharide (such as maltotriose, maltotetraose, maltopentaose, maltohexaose, and maltoheptaose), maltose, sucrose acetate isobutyrate, dextrose, erythrose, erythrulose, deoxyribose, gulose, ketotriose, lactose, lactulose, kestose, nystose, mannose, sucralose, palatinose, polydextrose, sorbose, sugaridextrose (blended sugar), or talose, or combinations of any two or more of the aforementioned sweeteners.

The sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, iso-maltulose, maltodextrin, and the like, and sugar alcohols or any other carbohydrates or combinations thereof capable of being reduced which do not adversely affect taste.

The sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green stevia powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet stevia-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer* mono), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falernum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners.

One of skill in the art will recognize that any one or more of any of the aforementioned sweeteners can be combined in various ratios, amounts, or concentrations to yield a sweetener alone or a combination of two or more sweeteners, which is then combined with one or more flavor modifying compound.

One of skill in the art will recognize that the aforementioned sweeteners for use in a formulation comprising one or more sweetener and one or more flavor modifying compound are provided by way of example and are not intended to be limiting.

Ingestible Compositions

In some embodiments, compounds as disclosed and described herein, individually or in combination, can be used for one or more methods such as modifying receptor function associated with chemosensory or chemosensory related sensation or reaction. Some embodiments provide a method of modulating a chemosensory receptor that includes modulating the activity, structure, function, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g.; gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ.

In general, compounds as disclosed and described herein, individually or in combination, can be provided in a composition, such as, e.g., an ingestible composition. In one embodiment, compounds as disclosed and described herein, individually or in combination, can impart a more sugar-like temporal profile and/or flavor profile to a sweetener composition by combining one or more of the compounds as disclosed and described herein with one or more sweeteners in the sweetener composition. In another embodiment, compounds as disclosed and described herein, individually or in combination, can increase or enhance the sweet taste of a composition by contacting the composition thereof with the compounds as disclosed and described herein to form a modified composition. In another embodiment, compounds as disclosed and described herein, individually or in combination, can be in a composition that modulates the sweet receptors and/or their ligands expressed in the body other than in the taste buds.

Some embodiments provide an ingestible composition, comprising the compound of any one of formulas (I), (Ia), (II) and (IIa), and a sweetener. In some embodiments, the composition further comprises a vehicle. In some embodiments, the vehicle is water. In some embodiments, the compound may be present at a concentration at or below its sweetness recognition threshold. In some embodiments, the sweetener is present in an amount from about 0.1% to about 12% by weight. In some embodiments, the sweetener is present in an amount from about 0.2% to about 10% by weight. In some embodiments, the sweetener is present in an amount from about 0.3% to about 8% by weight. In some embodiments, the sweetener is present in an amount from about 0.4% to about 6% by weight. In some embodiments, the sweetener is present in an amount from about 0.5% to about 5% by weight. In some embodiments, the sweetener is present in an amount from about 1% to about 2% by weight. In some embodiments, the sweetener is present in an amount from about 0.1% to about 5% by weight. In some embodiments, the sweetener is present in an amount from about 0.1% to about 4% by weight. In some embodiments, the sweetener is present in an amount from about 0.1% to about 3% by weight. In some embodiments, the sweetener is present in an amount from about 0.1% to about 2% by weight. In some embodiments, the sweetener is present in an amount from about 0.1% to about 1% by weight. In some embodiments, the sweetener is present in an amount from about 0.1% to about 0.5% by weight. In some embodiments, the sweetener is present in an amount from about 0.5% to about 10% by weight. In some embodiments, the sweetener is present in an amount from about 2% to about 8% by weight. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose. In some embodiments, the sweetener is rebaudiosode A or other sweet Stevia-based glycosides, such as glucosylated steviol glycosides.

In some embodiments, an ingestible composition may be a beverage. In some embodiments, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In some embodiments, one or more compounds as described herein and one or more sweetener as described herein may be included in a food or beverage product, wherein the food or beverage product may additionally comprise:

acids, including, for example citric acid, phosphoric acid, ascorbic acid, sodium acid sulfate, lactic acid, or tartaric acid;

bitter ingredients, including, for example caffeine, quinine, green tea, catechins, polyphenols, green robusta coffee extract, green coffee extract, whey protein isolate, or potassium chloride;

coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;

preservatives, including, for example sodium benzoate, potassium benzoate, potassium sorbate, sodium metabisulfate, sorbic acid, or benzoic acid;

antioxidants including, for example ascorbic acid, calcium disodium EDTA, alpha tocopherols, mixed tocopherols, rosemary extract, grape seed extract, resveratrol, or sodium hexametaphosphate;

vitamins or functional ingredients including, for example resveratrol, Co-Q10, omega 3 fatty acids, theanine, choline chloride (citocoline), fibersol, inulin (chicory root), taurine, panax ginseng extract, guanana extract, ginger extract, L-phenylalanine, L-carnitine, L-tartrate, D-glucoronolactone, inositol, bioflavonoids, *Echinacea*, ginko biloba, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;

clouding agents, including, for example ester gun, brominated vegetable oil (BYO), or sucrose acetate isobutyrate (SAIB);

buffers, including, for example sodium citrate, potassium citrate, or salt;

flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), or carrageenan.

Some embodiments provide a method of enhancing sweetness of a sweetener, comprising combining a compound of any one of formulas (I), (Ia), (II) and (IIa) with the sweetener. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In one embodiment, compounds as disclosed and described herein, individually or in combination, can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment, compounds as disclosed and described herein, individually or in combination, can enhance the sweetness of a sweetener under a broad range of pH, e.g., from lower pH to neutral pH. The lower and neutral pH includes, but is not limited to, a pH from about 2.5 to about 8.5; from about 3.0 to about 8.0; from about 3.5 to about 7.5; and from about 4.0 to about 7. In certain embodiments, compounds as disclosed and described herein, individually or in combination, can enhance the perceived sweetness of a fixed concentration of a sweetener in taste tests at a compound concentration of about 50 µM, 40 µM, 30 µM, 20 µM, or 10 µM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener is sucralose.

Some embodiments provide supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products including compounds as disclosed and described herein, individually or in combination.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In some embodiments, compounds as disclosed and described herein, individually or in combination may be included in food or beverage products or formulations. Examples of food and beverage products or formulations include, but are not limited to sweet coatings, frostings, or glazes for ingestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for ingestible compositions, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of sweeteners so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

In some embodiments, compounds as disclosed and described herein, individually or in combination, modulate the sweet taste or other taste properties of other natural or synthetic sweet tastants, and ingestible compositions made therefrom. In one embodiment, the compounds as disclosed and described herein, individually or in combination, may be used or provided in its ligand enhancing concentration(s). For example, the compounds as disclosed and described herein, individually or in combination, may be present in an amount of from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

Some embodiments provide a sweet enhancing composition. The sweet enhancing composition comprises a compound of the present invention in a sweet flavor enhancing amount in combination with a first amount of sweetener, wherein the sweetening is more than the sweetening provided by the first amount of sweetener without the compound. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, provide enhancement of potency of a sweetener at the T1R2/T1R3 taste receptor as measured by an enhancement ratio, defined as the ratio of $EC_{50}$ of the sweetener with and without the compound described herein. In some embodiments, compounds as disclosed and described herein, individually or in combination, provide enhancement ratio of greater than 1 and less than 10. In some embodiments, compounds as disclosed and described herein, individually or in combination, provide an enhancement ratio from 10 to 20. In some embodiments, compounds as disclosed and described herein, individually or in combination, provide an enhancement ratio greater than 20. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arbinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arbinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Therapeutic Utilities

In some embodiments, compounds as disclosed and described herein, individually or in combination can be used for therapeutic purpose such as modulating a chemosensory receptor and/or its ligand to achieve therapeutic effect. For example, the therapeutic purpose may include modulating a chemosensory receptor and/or its ligand expressed in the body other than in the taste buds.

In some embodiments, a method of modulating a chemosensory receptor and/or its ligand includes modulating the expression, secretion, and/or functional level of T1R expressing cells associated with hormone, peptide, enzyme production by administering compounds as disclosed and described herein, individually or in combination to an individual in need thereof. In one example, the method of the present invention includes modulating the level of glucose, e.g., inhibitors or modulators of a chemosensory receptor such as T1R2/T1R3 can be used to decrease glucose level (e.g., glucose absorption) in a subject by administering compounds as disclosed and described herein, individually or in combination to an individual in need thereof. In some embodiments, the method includes modulating the level of incretins, e.g., agonists or enhancers of a chemosensory receptor such as T1R2/T1R3 can be used to increase glucagon-like peptide 1 (GLP-1) and thus increase the production of insulin by administering compounds as disclosed and described herein, individually or in combination to an individual in need thereof. In some embodiments, the method includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. by administering compounds as disclosed and described herein, individually or in combination to an individual in need thereof. In some embodiments, the method includes modulating the pathways associated with hormones, peptides, and/or enzymes secreted by T1R expressing cells by administering compounds as disclosed and described herein, individually or in combination to an individual in need thereof.

In some embodiments, the method includes modulating the activity of T1R (e.g., T1R1, T1R2, or T1R3) expressing cells, e.g., liver cells (e.g., hepatocytes, endothelial cells, Kupffer cells, Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin), D cells (delta cells, e.g., expressing somatostatin), I cells (e.g., expressing cholecystokinin (CCK), K cells (e.g., expressing gastric inhibitory polypeptide), P/D1 cells (e.g., expressing ghrelin), chief cells (e.g., expressing pepsin), and S cells (e.g., expressing secretin) by administering compounds as disclosed and described herein, individually or in combination to an individual in need thereof. In some embodiments, the method includes increasing the expression level of T1R in T1R expressing cells by administering compounds as disclosed and described herein, individually or in combination to an individual in need thereof. In some embodiments, the method includes increasing the secretion level of T1R expressing cells by administering compounds as disclosed and described herein, individually or in combination to an individual in need thereof.

In some embodiments, the method includes modulation, treatment, and/or prophylactic measure of a condition associated with the gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectal disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc. by administering compounds as disclosed and described herein, individually or in combination to an individual in need thereof.

In some embodiments, the method includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycemia, hyperlipoproteinemias, etc.

by administering compounds as disclosed and described herein, individually or in combination to an individual in need thereof.

In some embodiments, the method includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human by administering compounds as disclosed and described herein, individually or in combination to an individual in need thereof.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastrointestinal tract, cold sensation of extremities, difficulty in concentration, impatience, sleep disorder, headache, general malaise, palpitation, night sweat, anxiety, dizziness, vertigo, hot flash, excess sweating, depression, etc.

In some embodiments, the method includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. by administering compounds as disclosed and described herein, individually or in combination to an individual in need thereof. In general, such promotion can be achieved either directly or via increasing the secretion of a regulatory entity, e.g., hormones, etc. by administering compounds as disclosed and described herein, individually or in combination to an individual in need thereof.

In some embodiments, the method includes increasing one or more gastrointestinal functions of a subject, e.g., to improve the quality of life or healthy state of an individual by administering compounds as disclosed and described herein, individually or in combination.

Some embodiments provide a method for treating a respiratory tract infection including administering compounds as disclosed and described herein, individually or in combination to an individual in need thereof. In some embodiments, compounds as disclosed and described herein, individually or in combination can be used for inhibition of respiratory tract infections. Some embodiments provide a method for treating infertility including administering compounds as disclosed and described herein, individually or in combination to an individual in need thereof.

Some embodiments provide a pharmaceutical composition containing a therapeutically effective amount of one or more compounds as disclosed and described herein, or a salt, solvate, and/or prodrug thereof, optionally with a suitable amount of a pharmaceutically acceptable vehicle. In another embodiment, the pharmaceutical composition comprises a therapeutically effective amount of one or more compounds as disclosed and described herein, or a salt, solvate, and/or prodrug thereof; and a suitable amount of a pharmaceutically acceptable vehicle so as to provide the form for proper administration to a patient.

In one embodiment, when administered to a patient, the compounds as disclosed and described herein and the optional pharmaceutically acceptable vehicles are sterile. In one embodiment, water is a preferred vehicle when a compound as disclosed and described herein is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound as disclosed and described herein may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

In some embodiments, the pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule.

For topical administration a compound as disclosed and described herein may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, compounds as disclosed and described herein may be formulated in accordance with routine procedures as a pharmaceutical composition adapted for intravenous administration to human beings. Typically, compounds for intravenous administration are solutions in sterile isotonic aqueous buffer. For injection, a compound may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When a compound is administered by infusion, it can be dispensed, for example, with an infusion bottle containing sterile pharmaceutical grade water or saline. In some embodiments, an ampoule of sterile water for injection or saline can be provided so that the ingredients may be mixed prior to administration when a compound is administered by injection.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art.

In some embodiments, a compound as disclosed and described herein may also be formulated in rectal or vaginal pharmaceutical compositions such as suppositories or retention enemas, e.g., containing conventional suppository bases such as cocoa butter or other glycerides.

In addition to the formulations described previously, a compound as disclosed and described herein may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

A compound as disclosed and described herein, and/or pharmaceutical composition thereof, will generally be used in an amount effective to achieve the intended purpose. For use to treat or prevent diseases or disorders the compounds as disclosed and described herein and/or pharmaceutical compositions thereof, are administered or applied in a therapeutically effective amount.

In some embodiments, the dosage may be delivered in a pharmaceutical composition by a single administration, by multiple applications or controlled release. In some embodiments, the compounds as disclosed and described herein may be delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound as disclosed and described herein per kilogram body weight.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems.

In some embodiments, the dosage of a compound described herein will preferably be within a range of circulating concentrations that include an effective dose with little or no toxicity.

In certain embodiments, the compounds as disclosed and described herein and/or pharmaceutical compositions thereof can be used in combination therapy with at least one other agent. In some embodiments, a compound as disclosed and described herein and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Some exemplary synthetic methods for preparing the present compounds are illustrated in Scheme 1 below.

Scheme 1: Preparation of 5-Substituted 4-amino-1H-benzo[c][1,2,6]thiadiazine 2,2-dioxide A-I and A-II

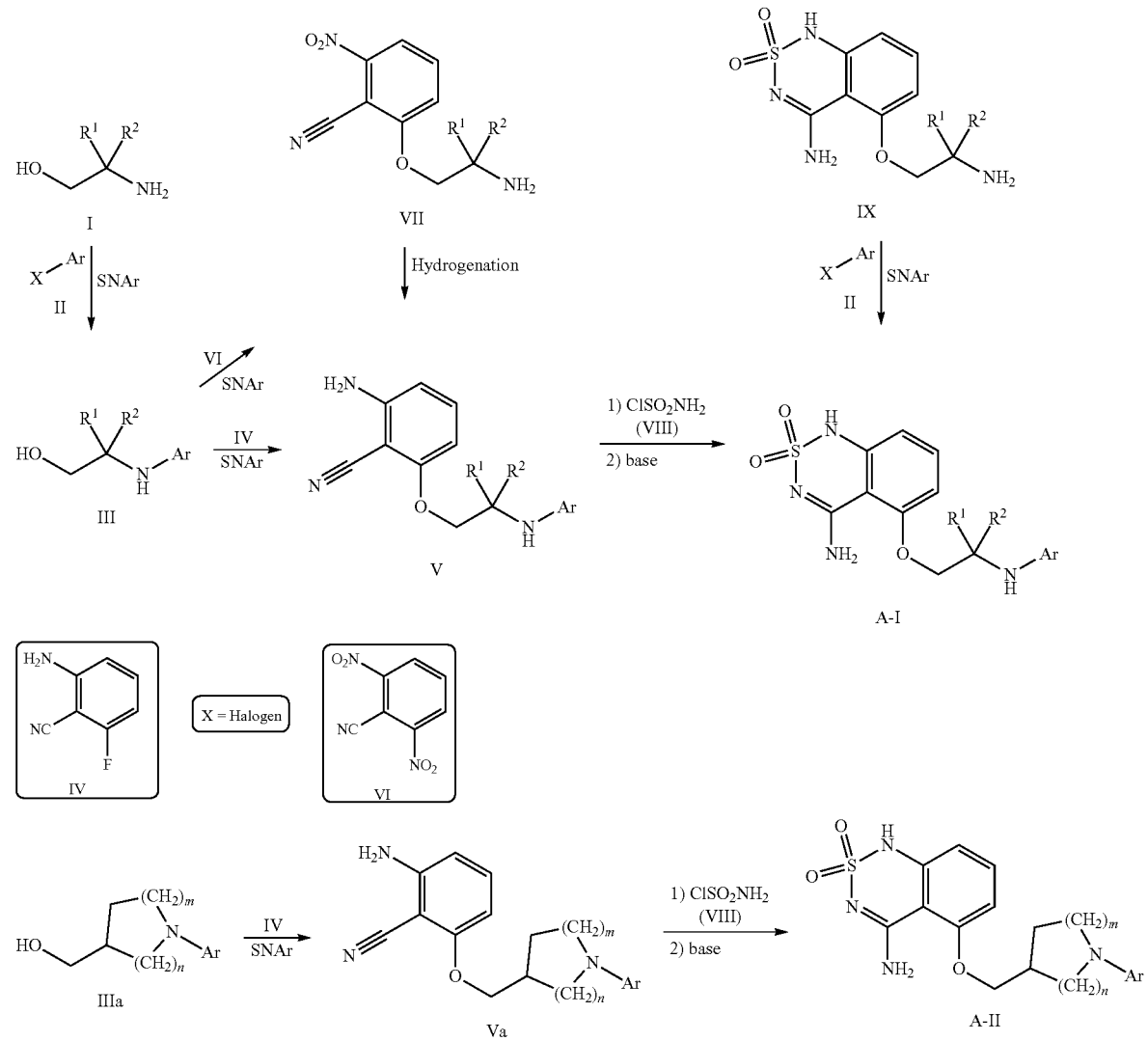

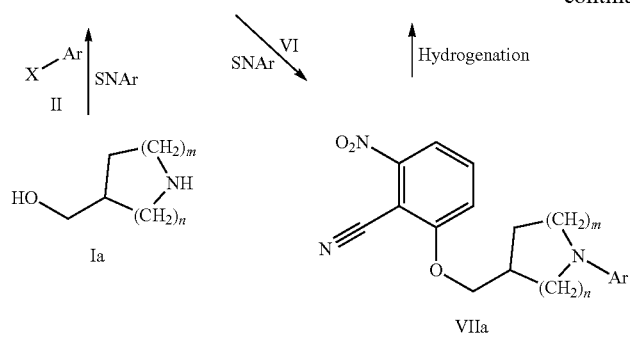
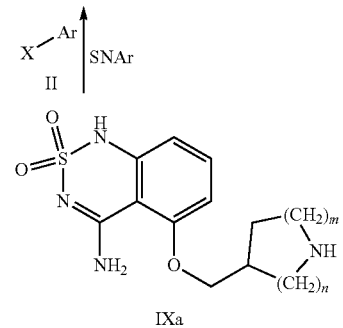

As shown in Scheme 1, alcohols III and IIIa which are, in some cases, commercially available building blocks for the synthesis of A-I and A-II can be easily synthesized by aromatic nucleophilic substitution between amino alcohols I respectively Ia and the corresponding aryl halide (II). Subsequently, aminobenzonitriles intermediates V respectively Va can be synthesized from 2-amino-6-fluorobenzonitrile (IV) and alcohols III respectively IIIa in the presence of a base such as NaH and tert-BuOK. Alternatively, the based induced reaction of 2,6-dinitrobenzonitrile (VI) and alcohols III respectively IIIa followed by simple nitro reduction of the intermediates 6-nitrobenzonitriles VII respectively VIIa can also yield the desired aminobenzonitriles intermediates V respectively Va. Ultimately aminobenzonitriles intermediates V and Va are treated with sulfamoyl chloride (VIII) under well controlled conditions followed by cyclization of the sulfamoyl intermediate under basic condition to afford the desired 5-Substituted 4-amino-1H-benzo[c][1,2,6]thiadiazine 2,2-dioxide A-I and A-II, respectively. Alternatively, 5-Substituted 4-amino-1H-benzo[c][1,2,6]thiadiazine 2,2-dioxide A-I and A-II can also be prepared from direct aromatic nucleophilic substitution between key building blocks IX respectively IXa and the corresponding aryl halides (II). The building blocks IX and IXa can be synthesized according to literature procedures for 4-amino-5-(piperidin-3-ylmethoxy)-1H-benzo[c][1,2,6]thiadiazine 2,2-dioxide.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1: 4-amino-5-(2-methyl-2-((5-methylpyrimidin-2-yl)amino)propoxy)-1H-benzo[c][1,2,6] thiadiazine 2,2-dioxide (100)

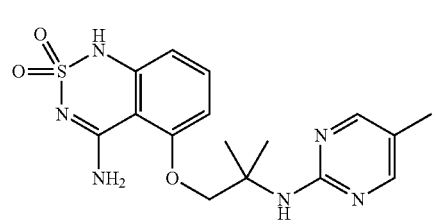

A solution of sulfamoyl chloride (0.526 g, 4.55 mmol, 2.25 equiv) in anhydrous acetonitrile (5 mL) was added at 0° C. to a mixture of 2-amino-6-(2-methyl-2-((5-methylpyrimidin-2-yl)amino)propoxy)benzonitrile (Example 1a, 0.600 g, 2.02 mmol, 1 equiv) and 2,6-dimethylpyridine (0.422 mL, 3.64 mmol, 1.8 equiv) in anhydrous acetonitrile (10 mL) under nitrogen. The mixture was allowed to warm up gradually to room temperature, stirred for 45 minutes, and quenched with acetic acid (0.23 mL, 2 equiv). The mixture was purified by HPLC (acetonitrile/water gradient) to provide the sulfamoyl intermediate; MS 377 (M+H$^+$). This intermediate was dissolved in EtOH (20 mL), treated with NaOH (3.33 M, 6 mL), and refluxed for 24 h. After cooling to room temperature, the mixture was concentrated, the residue dissolved in (10 mL), a acidified until pH 4.0. The precipitated product was collected by filtration and recrystallized from MeOH to provide the title compound as a white solid, 402 mg, 53% yield. 1H NMR (DMSO-d6, 400 MHz): 1.44 (s, 3H), 2.03 (s, 3H), 4.43 (s, 2H), 6.59 (d, J=8.0 Hz, 1H), 6.74 (d, J=8.4 Hz, 1H), 6.93 (s, 1H), 7.44 (t, J=8.0 Hz, 1H), 7.94 (s, 1H), 8.12 (s, 2H), 8.32 (s, 1H), 10.96 (s, 1H) ppm. MS=377 (MH$^+$).

Example 1a: 2-amino-6-(2-methyl-2-((5-methylpyrimidin-2-yl)amino)propoxy)-benzonitrile

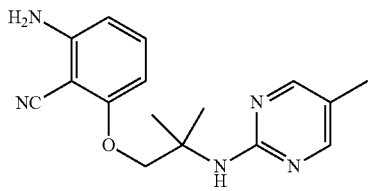

1a

Sodium hydride (0.154 g, 3.85 mmol, 1.5 equiv) was added to a mixture of 2-amino-6-fluorobenzonitrile (0.524 g, 3.85 mmol, 1.5 equiv) and 2-methyl-2-((5-methylpyrimidin-2-yl)amino)propan-1-ol (Example 1b, 0.465 g, 2.56 mmol, 1 equiv) in anhydrous THF (25 mL) under nitrogen. The reaction mixture was stirred for 10 minutes at room temperature and refluxed for 21 h. The reaction mixture was concentrated and the residue was purified by chromatography on a silica (50% EtOAc in Hexanes gradient) to provide the tithe compound (611 mg, 80% yield), MS 298 (MH+).

Example 1b: 2-methyl-2-((5-methylpyrimidin-2-yl)amino)propan-1-ol

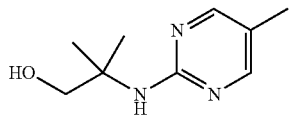

1b

A mixture of 2-amino-2-methylpropan-1-ol (1.60 g, 17.9 mmol, 2.3 equiv), 2-chloro-5-methylpyrimidine (1.00 g, 7.78 mmol, 1 equiv), and triethylamine (1.90 mL, 13.6 mmol, 1.75 equiv) was heated at 170° C. in a microwave for 2 hours. The product was purified by chromatography on silica (O % to 100% EtOAc in Hexanes gradient) to give the desired product as an oil that solidified slowly (469 mg, 33% yield) MS 182 (MH+).

Compounds in Table 1 were prepared in a similar manner as described above using the corresponding amino alcohols and halogenated heteroaryls that were either purchased or synthesized following known procedures.

TABLE 1

| Compound | Structure | MS (MH+) |
|---|---|---|
| 101 | | 362 |
| 102 | 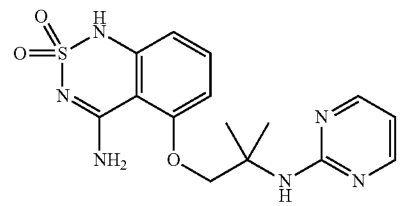 [SMILES: CC(C)(COc1cccc2c1C(N)=NS(=O)(=O)N2)Nc1ncccn1] | 363 |
| 103 | 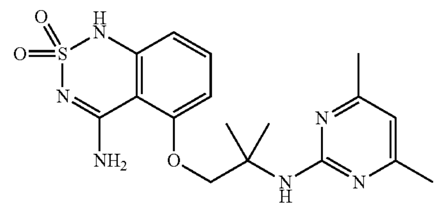 [SMILES: Cc1cc(C)nc(NC(C)(C)COc2cccc3c2C(N)=NS(=O)(=O)N3)n1] | 391 |
| 104 | 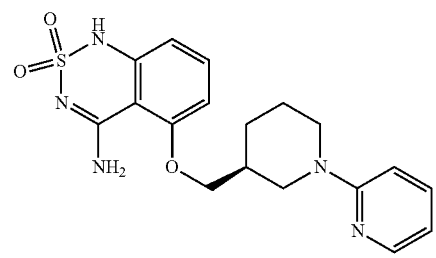 [SMILES: NC1=NS(=O)(=O)Nc2cccc(OC[C@H]3CCCN(c4ccccn4)C3)c21] | 388 |
| 105 | 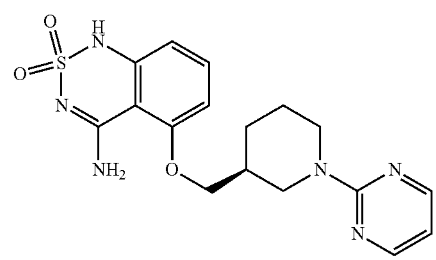 [SMILES: NC1=NS(=O)(=O)Nc2cccc(OC[C@H]3CCCN(c4ncccn4)C3)c21] | 389 |

Example 2: 4-amino-5-(2-((2-(1H-imidazol-1-yl)pyrimidin-4-yl)amino)-2-methylpropoxy)1H-benzo[c][1,2,6]thiadiazine 2,2-dioxide (200)

200

To a solution of 4-amino-5-(2-((2-chloropyrimidin-4-yl)amino)-2-methylpropoxy)-1H-benzo[c][1,2,6]thiadiazine 2,2-dioxide (Example 1a, 200 mg, 0.504 mmol) in dry DMA (3 mL) was added imidazole (69 mg, 1.01 mmol) and the solution was heated at 110° C. for 16 hours. The reaction was cooled to room temperature and purified by preparative HPLC (RPC-18, water/acetonitrile gradient). The clean fractions were concentrated and the material was recrystallized from EtOH/H₂O to afford the title compound (SID 59032259) as off white solid (119 mg, 55% yield). 1H NMR (400 MHz, d6-DMSO) δ 1.54 (s, 6H), 4.49 (s, 2H), 6.50 (d, J=6.0 Hz, 1H), 6.61 (dd, J=7.2 Hz, 0.6 Hz, 1H), 6.86 (dd, J=7.2 Hz, 1.2 Hz, 1H), 7.07 (m, 1H), 7.44 (t, J=8.4 Hz, 1H), 7.70 (br.s, 1H), 7.80 (t, J=1.2 Hz, 1H), 7.95 (br.s, 1H), 8.05 (d, J=6.0 Hz, 1H), 8.41 (br.s, 1H), 8.44 (t, J=1.2 Hz, 1H), 11.00 (s, 1H). MS 429 (MH⁺).

Example 2a: 4-amino-5-(2-((2-chloropyrimidin-4-yl)amino)-2-methylpropoxy)-1H-benzo[c][1,2,6]thiadiazine 2,2-dioxide (201)

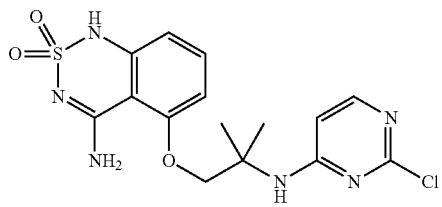

201

To a solution of 4-amino-5-(2-amino-2-methylpropoxy)-1H-benzo[c][1,2,6]thiadiazine 2,2-dioxide hydrochloride (US 20150376176 A1) (2.00 g, 6.23 mmol) in dry DMF (30 mL) was added DIEA (30 mL) was added DIEA (3.26 mL, 18.7 mmol). After stirring for 5 min of at room temperature, 2,4-dichloropyrimidine (2.79 g, 18.7 mmol) was added and the solution was heated at 110° C. for 16 hours. The reaction was cooled to room temperature and water was added until the solution became cloudy. 12.5 mL of 2N NaOH solution were added and the solution was stirred at room temperature for 30 min and washed with DCM. The aqueous layer was cooled in an ice bath and acidified with 1N HCl until pH=3 and the resulting precipitate was collected by vacuum filtration and washed with water. The solid was collected, dried, and purified by silica gel chromatography using a 50-100% gradient of EtOAc in Hexanes as eluent to afford the title compound as a pale orange solid (822 mg, 33% yield). 1H NMR (400 MHz, d6-DMSO) δ 1.48 (s, 6H), 4.39 (s, 2H), 6.53 (d, J=4.0 Hz, 1H), 6.62 (dd, J=8.0 Hz, 1H), 6.80 (dd, J=8.0 Hz, 1H), 7.47 (t, J=8.0 Hz, 1H), 7.65 (br.s, 1H), 7.93 (d, J=8.0 Hz, 1H), 7.99 (s, 1H), 8.39 (br.s, 1H), 11.02 (s, 1H). MS 397 (MH+).

Compounds in Table 2 were prepared in a similar manner as described above using amines that were either purchased or synthesized following known procedures.

TABLE 2

| Compound | Structure | MS (MH⁺) |
|---|---|---|
| 202 | (structure) | 429 |
| 203 | (structure) | 422 |
| 204 | (structure) | 432 |

TABLE 2-continued

| Compound | Structure | MS (MH+) |
|---|---|---|
| 205 | 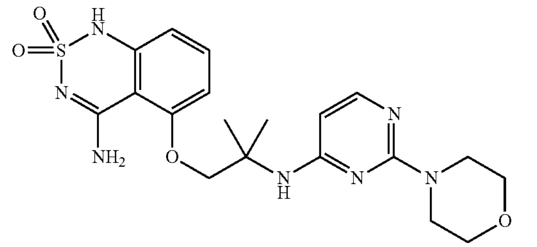 [SMILES: CC(C)(COc1cccc2c1C(N)=NS(=O)(=O)N2)Nc1ccnc(N2CCOCC2)n1] | 448 |
| 206 | 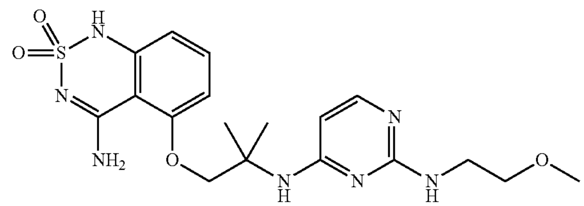 [SMILES: COCCNc1nccc(NC(C)(C)COc2cccc3c2C(N)=NS(=O)(=O)N3)n1] | 436 |
| 207 | 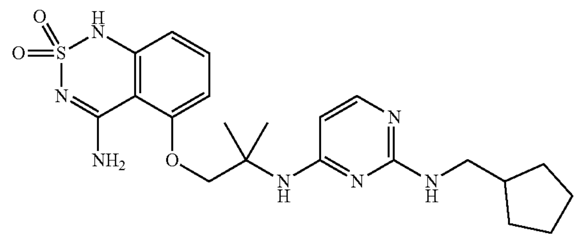 [SMILES: CC(C)(COc1cccc2c1C(N)=NS(=O)(=O)N2)Nc1ccnc(NCC2CCCC2)n1] | 460 |
| 208 | 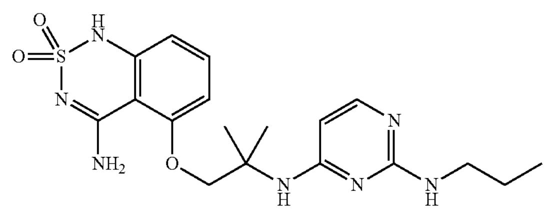 [SMILES: CCCNc1nccc(NC(C)(C)COc2cccc3c2C(N)=NS(=O)(=O)N3)n1] | 420 |

Example 3: (S)-4-amino-5-((1-(4,6-dimethylpyrimidin-2-yl)piperidin-3-yl)methoxy)-1H-benzo[c][1,2,6]thiadiazine 2,2-dioxide (300)

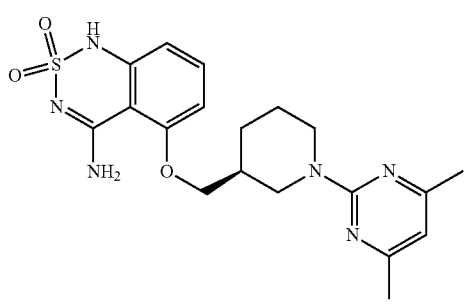

A solution of (S)-4-amino-5-(piperidin-3-ylmethoxy)-1H-benzo[c][1,2,6]thiadiazine 2,2-dioxide hydrochloride (Adamski-Werner et al., US 20140235624 A1) (1.00 g, 2.88 mmol) in DMA (15 mL) at room temperature was treated with TEA (0.80 mL, 5.77 mmol) and 2-chloro-4,6-dimethylpyrimidine (0.45 g, 3.17 mmol). The mixture was stirred for 15 hours at 120° C. Upon completion the mixture was diluted with water (50 mL). The solution was acidified with 1N HCl until pH=5-6. A solid precipitate was observed which filtered and washed with water. The solid product was dissolved in hot ethanol (50 mL) and filtered to remove any insoluble solids. The ethanol solution was then diluted with water (100 mL). A solid precipitate crystallized slowly to furnish the title compound as a tan solid (0.608 g, 1.46 mmol, 51% yield) $^1$H NMR (400 MHz, DMSO-$d_6$): δ 1.42 (m, 2H), 1.70 (m, 1H), 1.89 (m, 1H), 2.12 (m, 1H), 2.18 (s, 6H), 3.03 (dd, J=13.0, 9.5 Hz, 1H), 3.11 (m, 1H), 4.08 (m, 2H), 4.36 (dd, J=13.0, 3.5 Hz, 1H), 4.55 (dd, J=12.5, 4.8 Hz, 1H), 6.34 (s, 1H), 6.62 (d, J=7.6 Hz, 1H), 6.76 (d, J=7.9 Hz, 1H), 7.45 (t, J=8.3 Hz, 1H), 7.81 (s, 1H), 8.43 (s, 1H), 10.97 (s, 1H). MS 417 (M+11+).

Compounds in Table 3 were prepared in a similar manner as described in Examples 3 using (S)-4-amino-5-(piperidin-3-ylmethoxy)-1H-benzo[c][1,2,6]thiadiazine 2,2-dioxide hydrochloride (Tachdjian et al. WO 2014025706 A1) and the corresponding halogenated heteroaryls that were either purchased or synthesized following known procedures.

TABLE 3

| Compound | Structure | MS (MH+) |
|---|---|---|
| 301 | 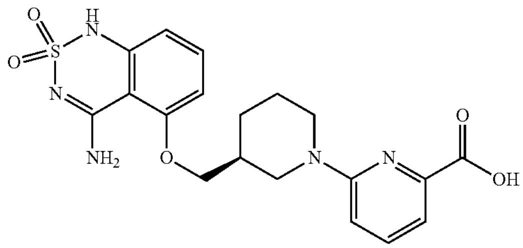 [SMILES: NC1=NS(=O)(=O)Nc2cccc(OC[C@H]3CCCN(c4cccc(C(=O)O)n4)C3)c21] | 432 |
| 302 | 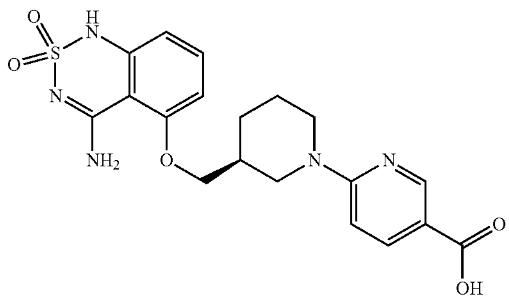 [SMILES: NC1=NS(=O)(=O)Nc2cccc(OC[C@H]3CCCN(c4ccc(C(=O)O)cn4)C3)c21] | 432 |
| 303 | 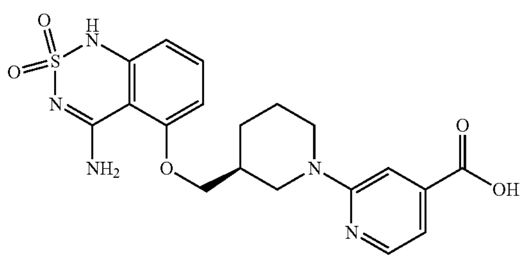 [SMILES: NC1=NS(=O)(=O)Nc2cccc(OC[C@H]3CCCN(c4cc(C(=O)O)ccn4)C3)c21] | 432 |
| 304 | 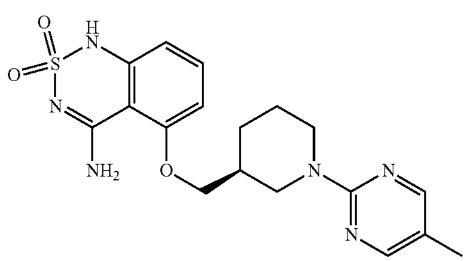 [SMILES: Cc1cnc(N2CCC[C@H](COc3cccc4c3C(N)=NS(=O)(=O)N4)C2)nc1] | 403 |
| 305 | 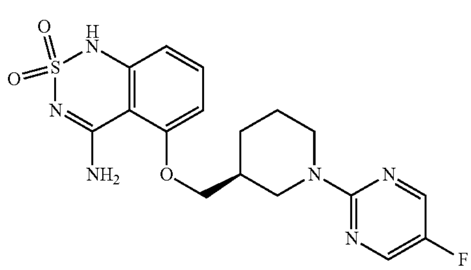 [SMILES: NC1=NS(=O)(=O)Nc2cccc(OC[C@H]3CCCN(c4ncc(F)cn4)C3)c21] | 407 |

TABLE 3-continued

| Compound | Structure | MS (MH+) |
|---|---|---|
| 306 | 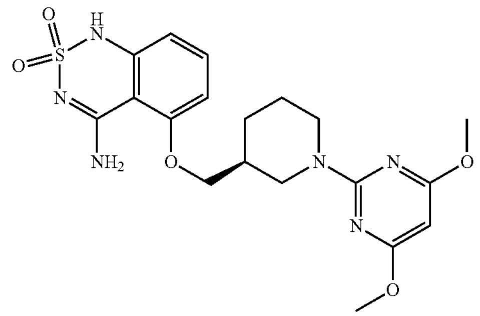 [SMILES: COc1cc(OC)nc(N2CCC[C@H](COc3cccc4c3C(N)=NS(=O)(=O)N4)C2)n1] | 449 |
| 307 | 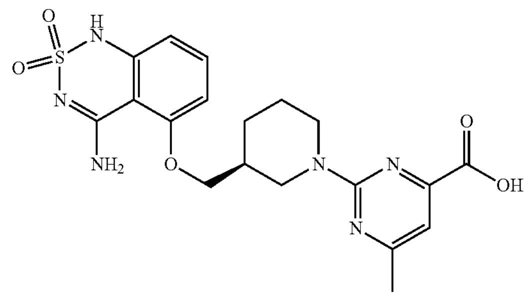 [SMILES: Cc1cc(C(=O)O)nc(N2CCC[C@H](COc3cccc4c3C(N)=NS(=O)(=O)N4)C2)n1] | 447 |

Example 4: (S)-6-(3-(((4-amino-2,2-dioxido-1H-benzo[c][1,2,6] thiadiazin-5-yl)oxy)methyl)piperidin-1-yl)-N-cyclopropylpicolinamide (400)

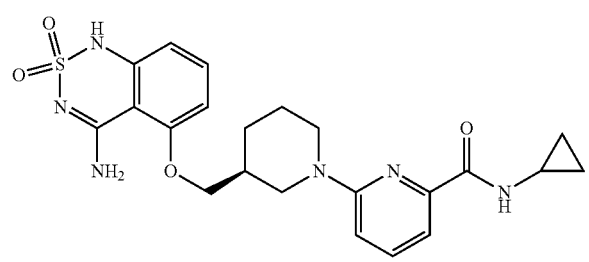

400

To a solution of (S)-6-(3-(((4-amino-2,2-dioxido-1H-benzo[c][1,2,6]thiadiazin-5-yl)oxy)methyl)piperidin-1-yl) picolinic acid (compound 301) (1.00 g, 2.32 mmol) in DMF (15 mL) at room temperature was treated with EDCI-HCl (0.47 g, 2.43 mmol), HOBt-H2O (0.33 g, 2.43 mmol), TEA (0.97 mL, 6.95 mmol), and cyclopropanamine (0.18 mL, 2.56 mmol). The mixture was stirred for 48 h at room temperature, diluted with dichloromethane (50 mL), washed with 1N HCl (25 mL), H2O 2O (25 mL), and brine (25 mL). The combined organic layers were dried over Na$_2$SO$_4$, filtered, and concentrated. The crude product was purified by prep HPLC (acetonitrile/H$_2$O). The resulting solid was recrystallized from ethanol and water to furnish the title compound as a tan solid (0.152 g, 0.39 mmol, 13%). 1H NMR (400 MHz, DMSO-d6): δ 0.61 (m, 2H), 0.71 (m, 2H), 1.45 (m, 2H), 1.75 (m, 1H), 1.90 (m, 1H), 2.19 (m, 1H), 2.77 (m, 1H), 2.92 (dd, J=13.1, 10.8 Hz, 2H), 4.13 (m, 2H), 4.29 (d, J=13.0 Hz, 2H), 6.63 (d, J=8.1 Hz, 1H), 6.78 (d, J=8.2 Hz, 1H), 6.96 (d, J=8.6 Hz, 1H), 7.23 (d, J=7.1 Hz, 1H), 7.47 (t, J=8.3 Hz, 1H), 7.66 (t, J=8.6 Hz, 1H), 7.81 (s, 1H), 8.21 (d, J=4.0 Hz, 1H), 8.41 (s, 1H), 10.98 (s, 1H). MS 471 (M+H+).

Compounds in Table 4 were prepared in a similar manner as described in Example 4 from compound 301 and the corresponding amines that were either commercially available or prepared using known procedures.

TABLE 4

| Compound | Structure | MS (MH+) |
|---|---|---|
| 401 | 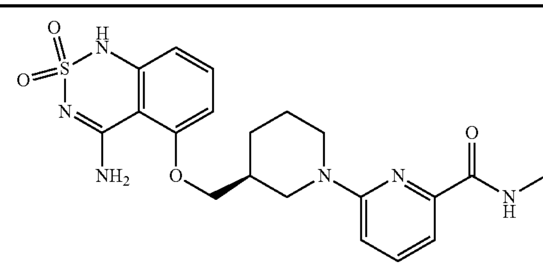 | 445 |

TABLE 4-continued

| Compound | Structure | MS (MH+) |
|---|---|---|
| 402 | 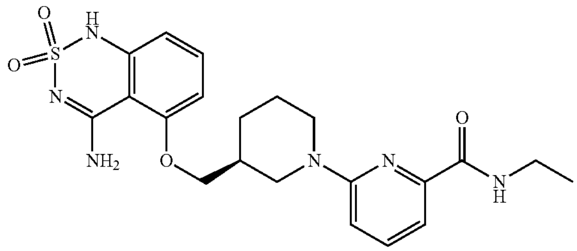 [SMILES: CCNC(=O)c1cccc(N2CCC[C@H](COc3cccc4c3C(N)=NS(=O)(=O)N4)C2)n1] | 459 |
| 403 | 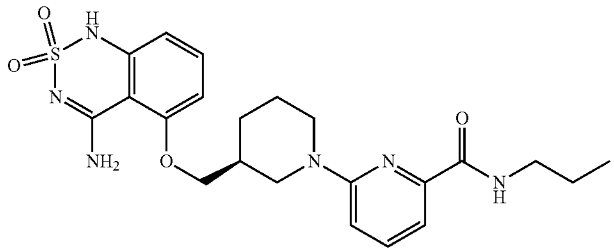 [SMILES: CCCNC(=O)c1cccc(N2CCC[C@H](COc3cccc4c3C(N)=NS(=O)(=O)N4)C2)n1] | 473 |
| 404 | | 475 |
| 405 | 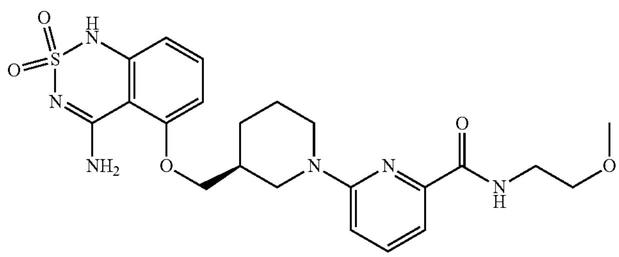 [SMILES: COCCNC(=O)c1cccc(N2CCC[C@H](COc3cccc4c3C(N)=NS(=O)(=O)N4)C2)n1] | 489 |
| 406 | 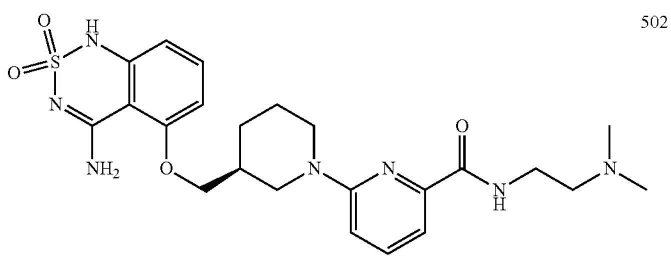 | 502 |
| 407 | 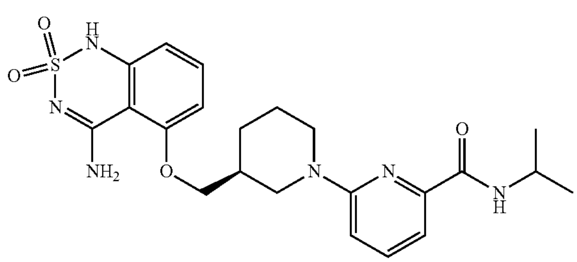 [SMILES: CC(C)NC(=O)c1cccc(N2CCC[C@H](COc3cccc4c3C(N)=NS(=O)(=O)N4)C2)n1] | 473 |
| 408 | 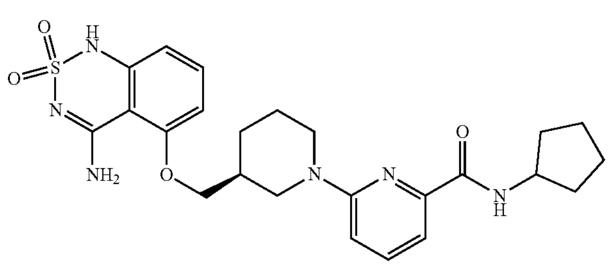 [SMILES: NC1=NS(=O)(=O)Nc2cccc(OC[C@H]3CCCN(c4cccc(C(=O)NC5CCCC5)n4)C3)c21] | 499 |

TABLE 4-continued

| Compound | Structure | MS (MH+) |
|---|---|---|
| 409 | 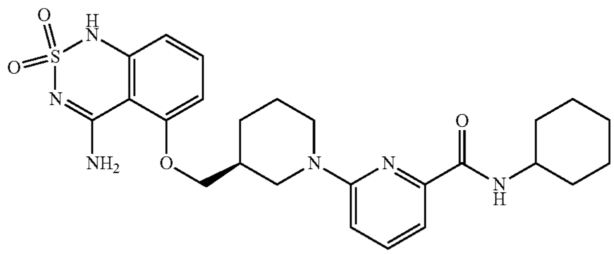 [SMILES: NC1=NS(=O)(=O)Nc2cccc(OC[C@H]3CCCN(c4cccc(C(=O)NC5CCCCC5)n4)C3)c21] | 513 |
| 410 | 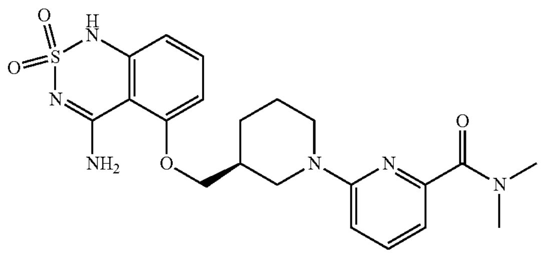 [SMILES: CN(C)C(=O)c1cccc(N2CCC[C@H](COc3cccc4c3C(N)=NS(=O)(=O)N4)C2)n1] | 459 |
| 411 | 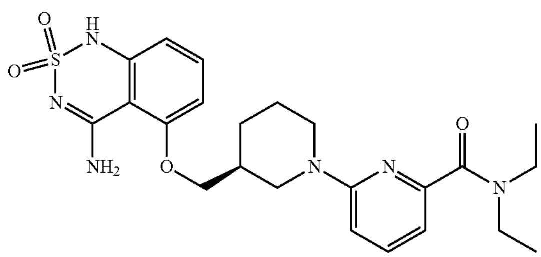 [SMILES: CCN(CC)C(=O)c1cccc(N2CCC[C@H](COc3cccc4c3C(N)=NS(=O)(=O)N4)C2)n1] | 487 |
| 412 | 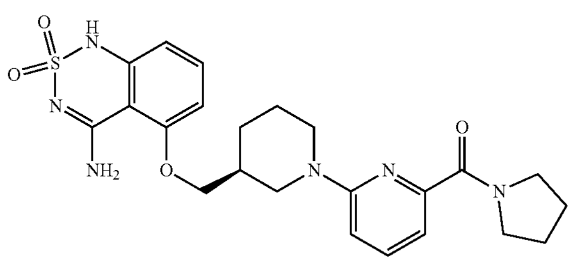 [SMILES: NC1=NS(=O)(=O)Nc2cccc(OC[C@H]3CCCN(c4cccc(C(=O)N5CCCC5)n4)C3)c21] | 485 |
| 413 | 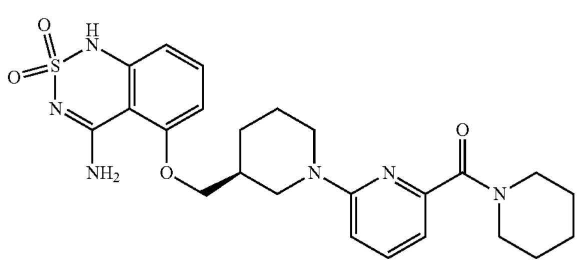 [SMILES: NC1=NS(=O)(=O)Nc2cccc(OC[C@H]3CCCN(c4cccc(C(=O)N5CCCCC5)n4)C3)c21] | 499 |
| 414 | 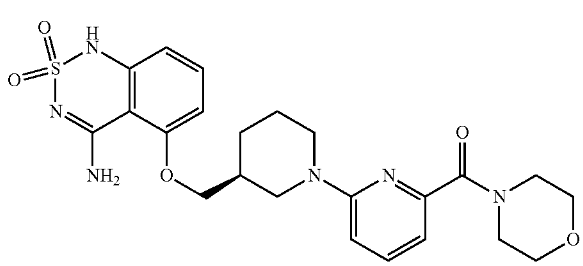 [SMILES: NC1=NS(=O)(=O)Nc2cccc(OC[C@H]3CCCN(c4cccc(C(=O)N5CCOCC5)n4)C3)c21] | 501 |

TABLE 4-continued

| Compound | Structure | MS (MH+) |
|---|---|---|
| 415 | 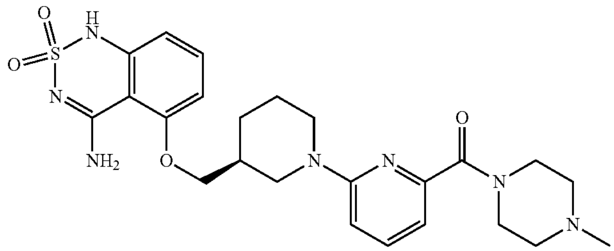 [SMILES: CN1CCN(C(=O)c2cccc(N3CCC[C@H](COc4cccc5c4C(N)=NS(=O)(=O)N5)C3)n2)CC1] | 514 |
| 416 | 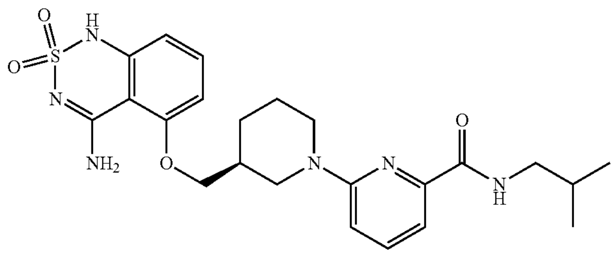 [SMILES: CC(C)CNC(=O)c1cccc(N2CCC[C@H](COc3cccc4c3C(N)=NS(=O)(=O)N4)C2)n1] | 487 |
| 417 | 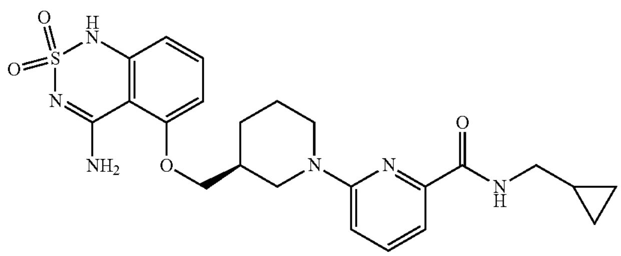 [SMILES: NC1=NS(=O)(=O)Nc2cccc(OC[C@H]3CCCN(c4cccc(C(=O)NCC5CC5)n4)C3)c21] | 485 |
| 418 | 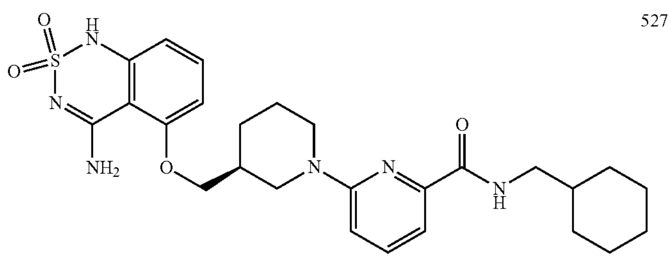 | 527 |

Compounds in Table 5 were prepared in a similar manner as described in Example 4 from compound 302 and the corresponding amines that were either commercially available or prepared using known procedures.

TABLE 5

| Compound | Structure | MS (MH+) |
|---|---|---|
| 500 | 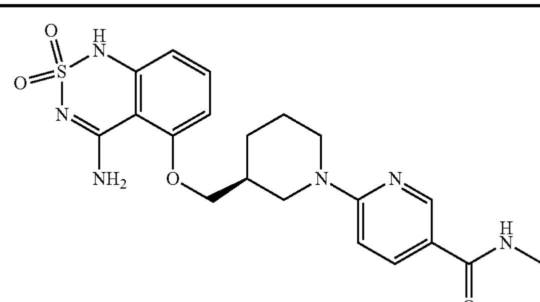 | 445 |

TABLE 5-continued

| Compound | Structure | MS (MH+) |
|---|---|---|
| 501 | 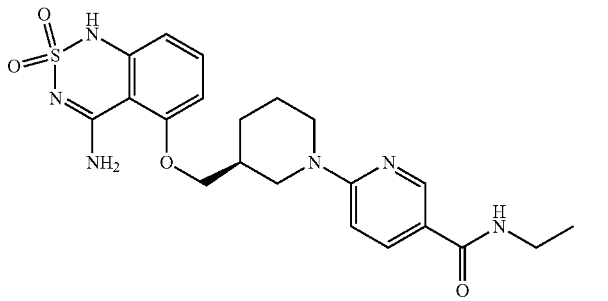 [SMILES: CCNC(=O)c1ccc(N2CCC[C@H](COc3cccc4c3C(N)=NS(=O)(=O)N4)C2)nc1] | 459 |
| 502 | 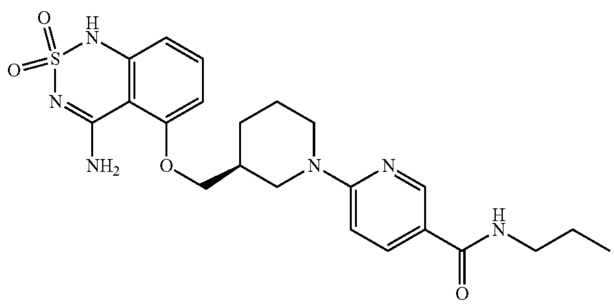 [SMILES: CCCNC(=O)c1ccc(N2CCC[C@H](COc3cccc4c3C(N)=NS(=O)(=O)N4)C2)nc1] | 473 |
| 503 | 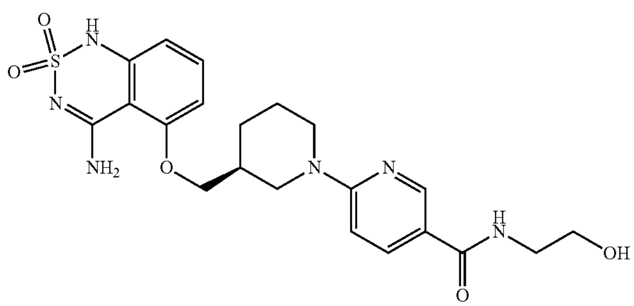 [SMILES: NC1=NS(=O)(=O)Nc2cccc(OC[C@H]3CCCN(c4ccc(C(=O)NCCO)cn4)C3)c21] | 475 |
| 504 | 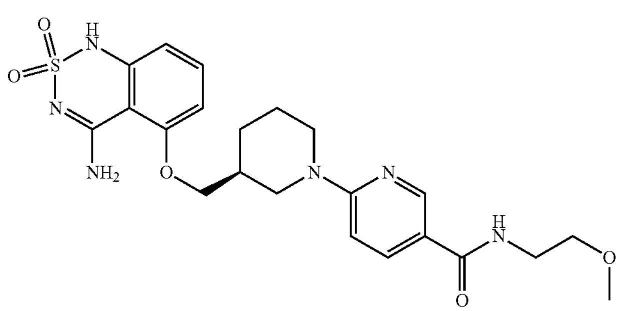 [SMILES: COCCNC(=O)c1ccc(N2CCC[C@H](COc3cccc4c3C(N)=NS(=O)(=O)N4)C2)nc1] | 489 |
| 505 | 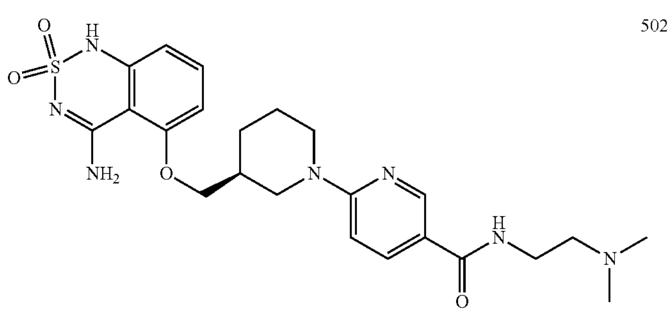 | 502 |

TABLE 5-continued

| Compound | Structure | MS (MH+) |
|---|---|---|
| 506 | 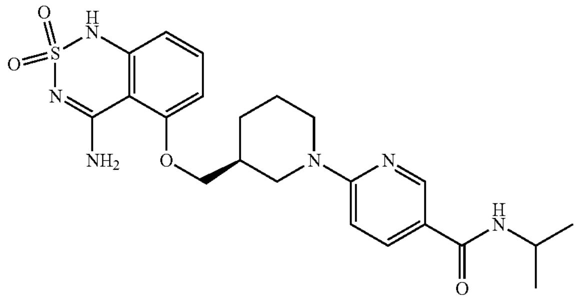 [SMILES: CC(C)NC(=O)c1ccc(N2CCC[C@H](COc3cccc4c3C(N)=NS(=O)(=O)N4)C2)nc1] | 473 |
| 507 | 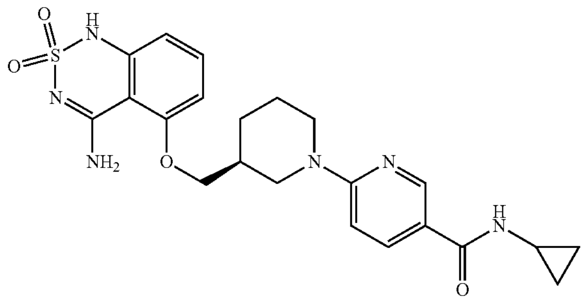 [SMILES: NC1=NS(=O)(=O)Nc2cccc(OC[C@H]3CCCN(c4ccc(C(=O)NC5CC5)cn4)C3)c21] | 471 |
| 508 | 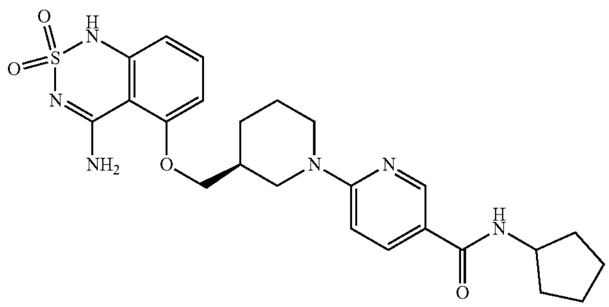 [SMILES: NC1=NS(=O)(=O)Nc2cccc(OC[C@H]3CCCN(c4ccc(C(=O)NC5CCCC5)cn4)C3)c21] | 499 |
| 509 | 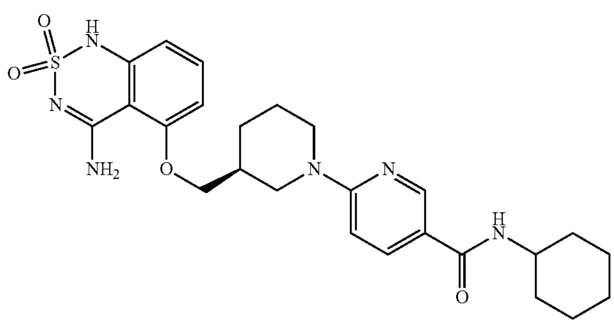 [SMILES: NC1=NS(=O)(=O)Nc2cccc(OC[C@H]3CCCN(c4ccc(C(=O)NC5CCCCC5)cn4)C3)c21] | 513 |
| 510 | 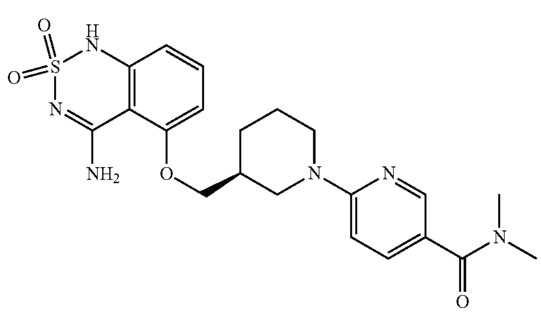 [SMILES: CN(C)C(=O)c1ccc(N2CCC[C@H](COc3cccc4c3C(N)=NS(=O)(=O)N4)C2)nc1] | 459 |

TABLE 5-continued

| Compound | Structure | MS (MH+) |
|---|---|---|
| 511 | 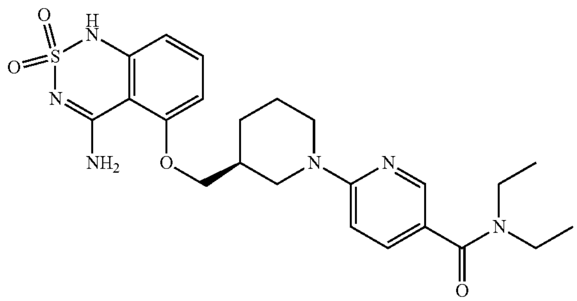 [SMILES: CCN(CC)C(=O)c1ccc(N2CCC[C@H](COc3cccc4c3C(N)=NS(=O)(=O)N4)C2)nc1] | 487 |
| 512 | 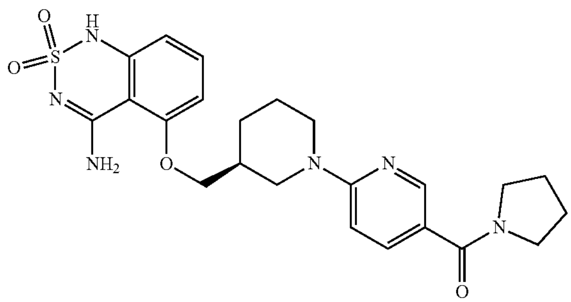 [SMILES: NC1=NS(=O)(=O)Nc2cccc(OC[C@H]3CCCN(c4ccc(C(=O)N5CCCC5)cn4)C3)c21] | 485 |
| 513 | 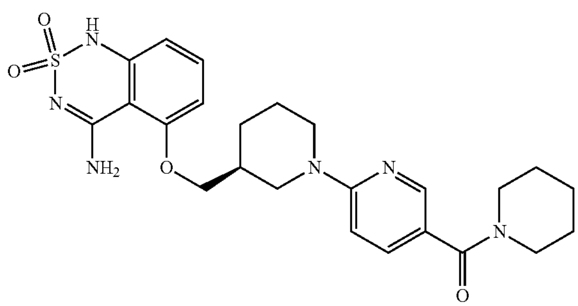 [SMILES: NC1=NS(=O)(=O)Nc2cccc(OC[C@H]3CCCN(c4ccc(C(=O)N5CCCCC5)cn4)C3)c21] | 499 |
| 514 | 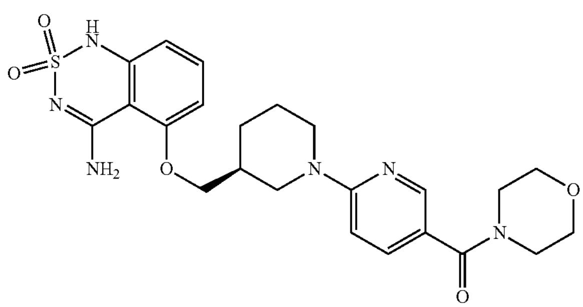 [SMILES: NC1=NS(=O)(=O)Nc2cccc(OC[C@H]3CCCN(c4ccc(C(=O)N5CCOCC5)cn4)C3)c21] | 501 |
| 515 | 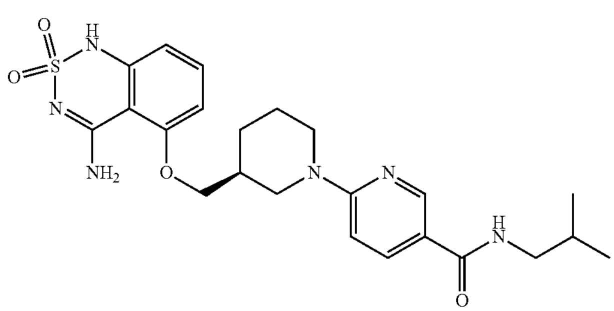 [SMILES: CC(C)CNC(=O)c1ccc(N2CCC[C@H](COc3cccc4c3C(N)=NS(=O)(=O)N4)C2)nc1] | 487 |

TABLE 5-continued

| Compound | Structure | MS (MH+) |
|---|---|---|
| 516 | 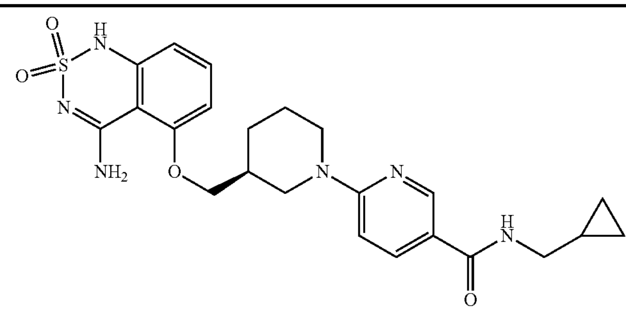 | 485 |
| 517 | 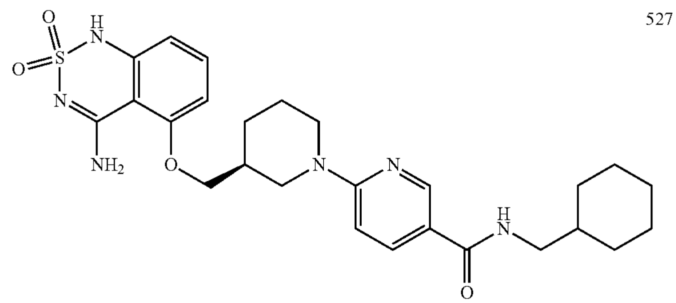 | 527 |

Compounds in Table 6 were prepared in a similar manner as described in Example 4 from compound 303 and the corresponding amines that were either commercially available or prepared using known procedures.

TABLE 6

| Compound | Structure | MS (MH+) |
|---|---|---|
| 600 | 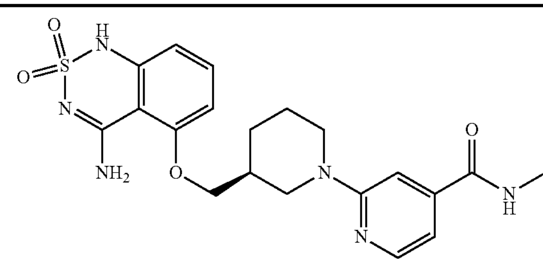 | 445 |
| 601 | 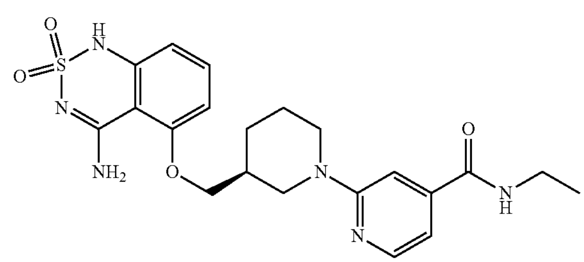 [SMILES: CCNC(=O)c1ccnc(N2CCC[C@H](COc3cccc4c3C(N)=NS(=O)(=O)N4)C2)c1] | 459 |
| 602 | 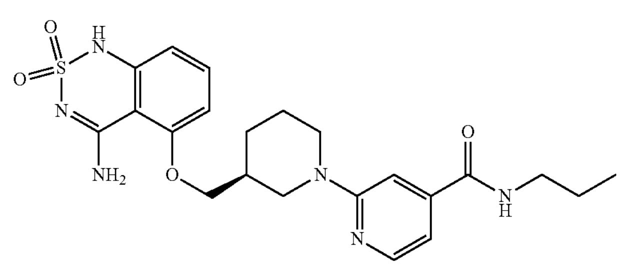 [SMILES: CCCNC(=O)c1ccnc(N2CCC[C@H](COc3cccc4c3C(N)=NS(=O)(=O)N4)C2)c1] | 473 |

TABLE 6-continued

| Compound | Structure | MS (MH+) |
|---|---|---|
| 603 | 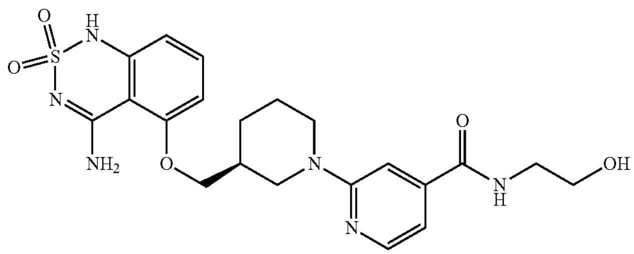 [SMILES: NC1=NS(=O)(=O)Nc2cccc(OC[C@H]3CCCN(c4cc(C(=O)NCCO)ccn4)C3)c21] | 475 |
| 604 | 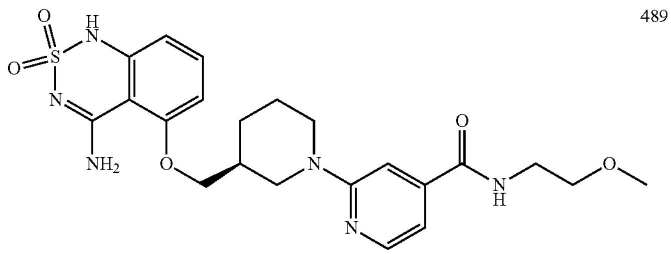 | 489 |
| 605 | 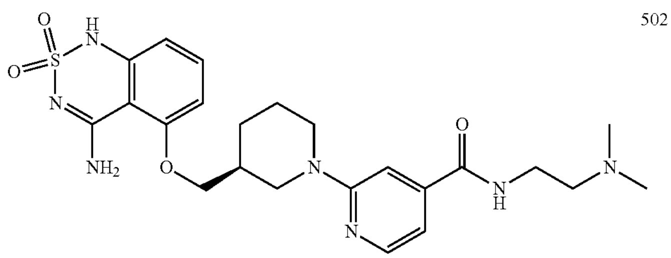 | 502 |
| 606 | 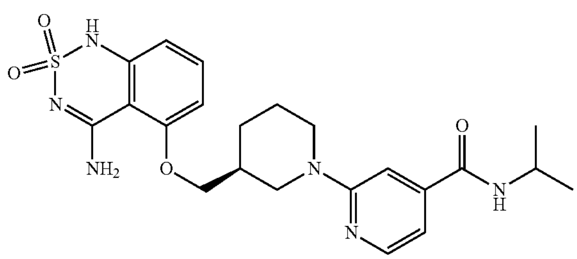 [SMILES: CC(C)NC(=O)c1ccnc(N2CCC[C@H](COc3cccc4c3C(N)=NS(=O)(=O)N4)C2)c1] | 473 |
| 607 | 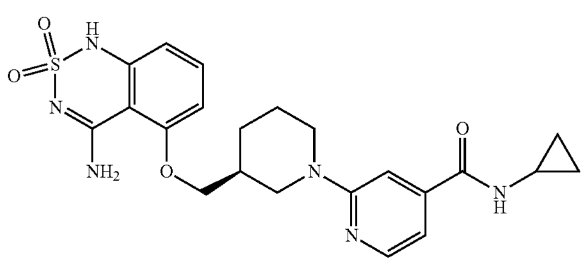 [SMILES: NC1=NS(=O)(=O)Nc2cccc(OC[C@H]3CCCN(c4cc(C(=O)NC5CC5)ccn4)C3)c21] | 471 |
| 608 | 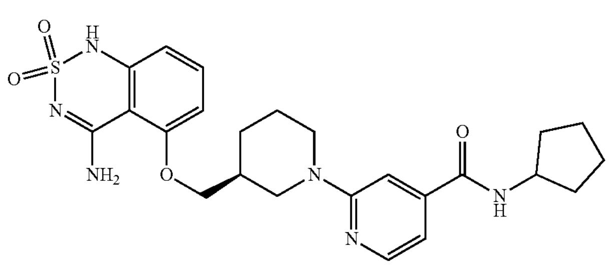 [SMILES: NC1=NS(=O)(=O)Nc2cccc(OC[C@H]3CCCN(c4cc(C(=O)NC5CCCC5)ccn4)C3)c21] | 499 |

TABLE 6-continued

| Compound | Structure | MS (MH+) |
|---|---|---|
| 609 | 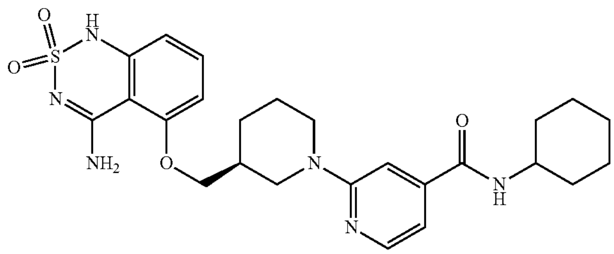 [SMILES: NC1=NS(=O)(=O)Nc2cccc(OC[C@H]3CCCN(c4cc(C(=O)NC5CCCCC5)ccn4)C3)c21] | 513 |
| 610 | 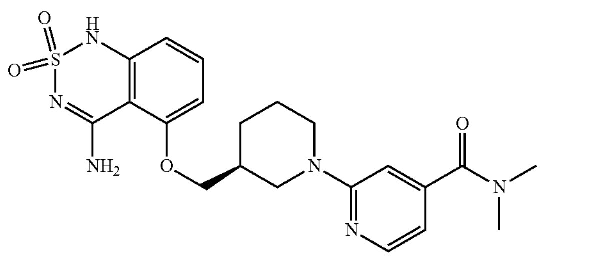 [SMILES: CN(C)C(=O)c1ccnc(N2CCC[C@H](COc3cccc4c3C(N)=NS(=O)(=O)N4)C2)c1] | 459 |
| 611 | 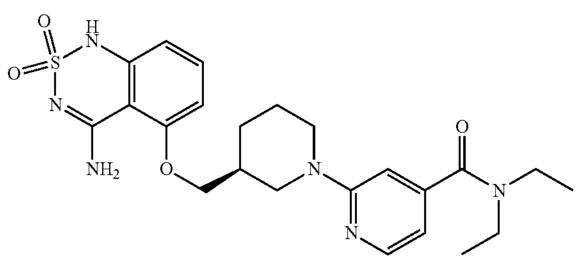 [SMILES: CCN(CC)C(=O)c1ccnc(N2CCC[C@H](COc3cccc4c3C(N)=NS(=O)(=O)N4)C2)c1] | 487 |
| 612 | 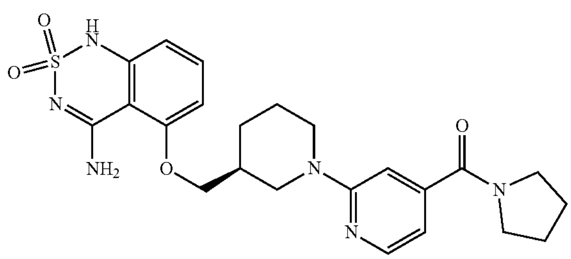 [SMILES: NC1=NS(=O)(=O)Nc2cccc(OC[C@H]3CCCN(c4cc(C(=O)N5CCCC5)ccn4)C3)c21] | 485 |
| 613 | 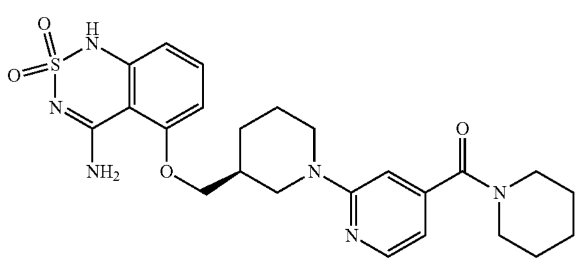 [SMILES: NC1=NS(=O)(=O)Nc2cccc(OC[C@H]3CCCN(c4cc(C(=O)N5CCCCC5)ccn4)C3)c21] | 499 |
| 614 | 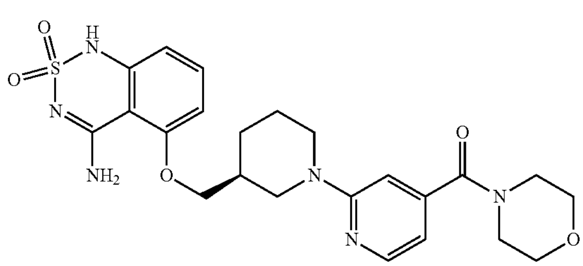 [SMILES: NC1=NS(=O)(=O)Nc2cccc(OC[C@H]3CCCN(c4cc(C(=O)N5CCOCC5)ccn4)C3)c21] | 501 |

TABLE 6-continued

| Compound | Structure | MS (MH+) |
|---|---|---|
| 615 | [structure] | 514 |
| 616 | [structure] | 487 |
| 617 | [structure] | 485 |
| 618 | [structure] | 527 |

Biological Examples

Example 5: Receptor-Based Assay

Potencies ($EC_{50}$ values) for the sweeteners sucrose, sucralose, and fructose were measured against the T1R2/T1R3 taste receptor. $EC_{50}$ was determined using the sweetener alone and in the presence of 3 μM, 10 μM, or 50 μM of test compound. $EC_{50}$ ratios were calculated by the ratio of potency with and without the test compound. The results are presented in Table 7. An "A" value indicates an enhancement ratio of greater than 20. A "B" value indicates an enhancement ratio from 10 to 20. A "C" value indicates an enhancement ratio greater than 1 and less than 10.

TABLE 7

| | Sucrose Enhancement $EC_{50}$ Ratio | | | Sucralose Enhancement $EC_{50}$ Ratio | | Fructose Enhancement $EC_{50}$ Ratio | |
|---|---|---|---|---|---|---|---|
| Compound | 3 μM | 10 μM | 50 μM | 10 μM | 50 μM | 10 μM | 50 μM |
| 100 | C | C | C | A | A | | |
| 101 | C | C | C | A | A | C | |
| 102 | | C | B | A | A | C | |
| 103 | C | C | C | A | A | C | C |
| 104 | C | C | C | A | A | C | |
| 105 | C | C | C | A | A | C | C |
| 200 | C | C | C | A | | | |
| 201 | C | C | C | | A | C | |
| 202 | | | C | | | | |
| 203 | | | | | | | |

TABLE 7-continued

| Compound | Sucrose Enhancement EC$_{50}$ Ratio | | | Sucralose Enhancement EC$_{50}$ Ratio | | Fructose Enhancement EC$_{50}$ Ratio | |
|---|---|---|---|---|---|---|---|
| | 3 µM | 10 µM | 50 µM | 10 µM | 50 µM | 10 µM | 50 µM |
| 204 | C | C | C | A | A | | C |
| 205 | C | C | C | B | A | | C |
| 206 | C | C | C | B | A | C | C |
| 207 | | | | | | | |
| 208 | C | C | C | A | A | C | C |
| 300 | C | C | C | A | A | | |
| 301 | C | C | C | A | A | | |
| 302 | C | C | C | A | A | C | C |
| 303 | C | C | C | C | A | | C |
| 304 | C | C | C | A | A | C | C |
| 305 | C | C | C | A | A | C | C |
| 306 | C | C | C | B | B | C | |
| 307 | C | C | C | A | A | C | C |
| 400 | C | C | B | A | A | C | C |
| 401 | C | B | C | A | A | | |
| 402 | C | C | C | A | A | | |
| 403 | C | C | C | A | A | C | |
| 404 | C | B | B | A | A | C | C |
| 405 | C | C | | B | | C | |
| 406 | C | B | B | A | | C | C |
| 407 | | B | C | | | C | C |
| 408 | C | B | B | A | A | | C |
| 409 | C | C | B | A | A | | |
| 410 | C | B | B | B | A | | C |
| 411 | C | C | | B | | | |
| 412 | C | C | B | A | A | C | C |
| 413 | C | C | C | B | A | | C |
| 414 | C | C | B | A | | C | C |
| 415 | C | C | C | | A | C | C |
| 416 | C | C | B | A | A | | C |
| 417 | C | C | C | A | A | | C |
| 418 | C | C | C | B | A | | |
| 500 | C | C | C | A | A | | |
| 501 | C | C | C | A | A | C | C |
| 502 | C | C | C | A | A | C | C |
| 503 | C | C | C | A | | | |
| 504 | C | C | C | A | A | | C |
| 505 | C | C | C | C | A | | C |
| 506 | C | C | C | A | A | | |
| 507 | C | C | C | A | A | | C |
| 508 | C | C | C | B | A | | C |
| 509 | C | C | C | B | A | | C |
| 510 | C | C | A | B | A | | C |
| 511 | C | C | B | A | A | | C |
| 512 | C | C | C | A | A | | C |
| 513 | C | C | C | A | A | C | C |
| 514 | C | C | C | A | B | C | C |
| 515 | C | C | C | A | A | C | C |
| 516 | C | C | C | A | A | | C |
| 517 | C | C | C | C | B | | |
| 600 | C | | B | A | A | | |
| 601 | | C | A | | | C | C |
| 602 | C | B | | A | A | C | C |
| 603 | C | B | C | A | | C | C |
| 604 | | | B | A | | | C |
| 605 | C | C | B | A | A | C | C |
| 606 | C | B | C | A | A | C | C |
| 607 | A | B | C | | | C | |
| 608 | C | C | B | A | A | C | C |
| 609 | C | C | C | B | B | C | C |
| 610 | | C | B | A | A | C | C |
| 611 | C | B | C | B | A | C | |
| 612 | C | C | C | A | A | C | C |
| 613 | | C | C | A | A | | |
| 614 | C | | A | A | A | | C |
| 615 | C | C | B | A | A | | |
| 616 | C | C | C | A | A | | C |
| 617 | C | C | C | A | A | C | C |
| 618 | C | C | C | B | B | | C |

Example 6: Sensory Experiments

Test samples containing either a sweetener (sucrose or high-fructose corn syrup) alone or in combination with a test compound were presented in pairs to a group of panelists who were asked to determine which of the samples was sweeter. Subjects refrained from eating or drinking (except water) for at least 1 hour prior to the test. Subjects rinsed with water several times to clean the mouth. The samples within a paired comparison test were presented in a randomized, counterbalanced order. Panelists had up to a 1 minute delay between taste tests to clear the mouth of any tastes. Binomial probability tables were used to determine the probability of the correct number of responses occurring for each test at alpha-0.05.

Stock solutions of test compounds were prepared at 1000× final concentration with ethanol to ensure dispersion in solution. Test compound samples including sucrose were prepared by diluting the stock solutions in a low sodium buffer (0.952 g of KCl, 5.444 g of $Na_2HPO_4$, and 0.952 g of $KH_2PO_4$ in deionized ultrafiltered water) at pH 7.1 and containing sucrose. Test compound samples including high fructose corn syrup were prepared by diluting the stock solutions in the low sodium buffer at pH 2.8 (using citric acid to adjust the pH) and containing high fructose corn syrup. Control samples were balanced to 0.1% ethanol final.

Table 8 presents the sensory results using sucrose as the sweetener. In samples containing the test compound, the test compound was present at a concentration of 10 ppm or less and the concentration of sucrose was 6%. This table indicates the sucrose-alone concentration having a perceived sweetness intensity equivalent to the sweetness intensity of the combination of test compound and sucrose. An "A" value indicates an equivalent sucrose concentration of 10% or greater. A "B" value indicates an equivalent sucrose concentration of greater than 6% and less than 10%.

TABLE 8

| Compound | Equivalent Sucrose Conc. |
|---|---|
| 200 | A |

Compound 200 was also tested using high-fructose corn syrup (HFCS) as the sweetener. In samples containing the test compound, the test compound was present at a concentration of 10 ppm or less and the concentration of HFCS was 6%. The sweetness intensity of the combination of test compound and 6% HFCS was found to be always greater than 6% HFCS-alone.

Compounds exhibiting T1R2/T1R3 agonist activity in the receptor-based assay were also evaluated to determine their inherent sweetness threshold. Compound 200 was also tested for inherent sweetness. It had sweetness intensity at 10 ppm that was less than the sweetness intensity of a 1.5% sucrose solution.

Although the invention has been described with reference to embodiments and examples, it should be understood that numerous and various modifications can be made without departing from the spirit of the invention. Accordingly, the invention is limited only by the following claims.

FURTHER EMBODIMENTS

1. A compound of formula (I):

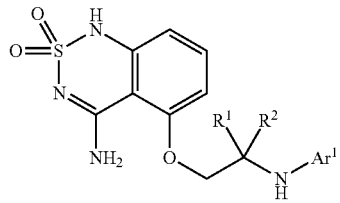

(I)

or a salt thereof, wherein:
$R^1$ and $R^2$ are each independently hydrogen or $C_{1-6}$ alkyl, or $R^1$ and $R^2$ together with the carbon to which they are attached is a $C_{3-7}$ carbocyclyl;
$Ar^1$ is an aryl or heteroaryl, each optionally substituted with one or more $R^3$;
each $R^3$ is independently selected from the group consisting of halo, cyano, nitro, oxo, —C(=O)$OR^{3A}$, —$NR^{3A}(CH_2)_pOR^{3B}$, —$NR^{3A}(CH_2)_pR^{3B}$, —$(CH_2)_qOR^{3B}$, —$(CH_2)_qR^{3B}$, —C(=O)$R^{3A}$, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, —C(=O)$NR^{3A}R^{3B}$, —$NR^{3A}$C(=O)$R^{3B}$, and $R^{3C}$;
each $R^{3A}$ is independently selected from the group consisting of hydrogen, halo, cyano, —$(CH_2)_qR^{3AA}$, —$(CH_2)_qN(R^{3AA})_2$, ($C_1$-$C_6$)alkyl, $C_{3-7}$ carbocyclyl, ($C_1$-$C_6$)alkoxy, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, heterocycle, aryl, heteroaryl, heterocycle($C_1$-$C_6$)alkyl, aryl($C_1$-$C_6$)alkyl, and heteroaryl($C_1$-$C_6$)alkyl;
each $R^{3B}$ is independently selected from the group consisting of hydrogen, halo, cyano, —$(CH_2)_qR^{3BB}$, —$(CH_2)_qN(R^{3BB})_2$, ($C_1$-$C_6$)alkyl, $C_{3-7}$ carbocyclyl, ($C_1$-$C_6$)alkoxy, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, heterocycle, aryl, heteroaryl, heterocycle($C_1$-$C_6$)alkyl, aryl($C_1$-$C_6$)alkyl, and heteroaryl($C_1$-$C_6$)alkyl;
each $R^{3C}$ is independently selected from the group consisting of ($C_1$-$C_6$)alkyl, ($C_1$-$C_6$)alkoxy, heterocycle, aryl, heteroaryl, heterocycle($C_1$-$C_6$)alkyl, aryl($C_1$-$C_6$)alkyl, heteroaryl($C_1$-$C_6$)alkyl, and $C_{3-7}$ carbocyclyl, each optionally substituted with one or more $R^{3CC}$;
each $R^{3AA}$ is independently selected from the group consisting of ($C_1$-$C_6$)alkyl, ($C_1$-$C_6$)alkoxy, heterocycle, aryl, heteroaryl, heterocycle($C_1$-$C_6$)alkyl, aryl($C_1$-$C_6$)alkyl, and $C_{3-7}$ carbocyclyl, each optionally substituted with one or more $R^{3CC}$;
each $R^{3BB}$ is independently selected from the group consisting of ($C_1$-$C_6$)alkyl, ($C_1$-$C_6$)alkoxy, heterocycle, aryl, heteroaryl, heterocycle($C_1$-$C_6$)alkyl, aryl($C_1$-$C_6$)alkyl, and $C_{3-7}$ carbocyclyl, each optionally substituted with one or more $R^{3CC}$;
each $R^{3CC}$ is independently selected from the group consisting of halo, cyano, ($C_1$-$C_6$)alkyl, ($C_1$-$C_6$)alkoxy, heterocycle, aryl, heteroaryl, heterocycle($C_1$-$C_6$)alkyl, aryl($C_1$-$C_6$)alkyl, and $C_{3-7}$ carbocyclyl;
each p is independently an integer selected from 1, 2, and 3; and
each q is independently an integer selected from 0, 1, 2 and 3.

2. The compound of Embodiment 1, which is a compound of formula (Ia):

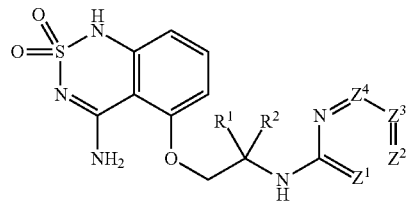

(Ia)

or a salt thereof, wherein:
$Z^1$ is —CH—, —$CR^3$—, or N (nitrogen);
$Z^2$ is —CH— or —$CR^3$—;
$Z^3$ is —CH—, —$CR^3$—, or N (nitrogen); and
$Z^4$ is —CH— or —$CR^3$—.

3. The compound of Embodiment 2, wherein $Z^1$ is —CH—.

4. The compound of Embodiment 2, wherein $Z^1$ is N (nitrogen).

5. The compound of Embodiment 2, wherein $Z^3$ is —CH—.

6. The compound of Embodiment 2, wherein $Z^3$ is N (nitrogen).

7. The compound of any one of Embodiments 2-6, wherein at least one of $Z^2$ and $Z^4$ is —$CR^3$—.

8. The compound of Embodiment 7, wherein:
each $R^3$ is independently selected from the group consisting of halo, —$NR^{3A}(CH_2)_pOR^{3B}$, —$NR^{3A}(CH_2)_pR^{3B}$, —$(CH_2)_qOR^{3B}$, —$(CH_2)_qR^{3B}$ and $R^{3C}$;
each $R^{3A}$ is independently selected from the group consisting of hydrogen, and ($C_1$-$C_6$)alkyl;
each $R^{3B}$ is independently selected from the group consisting of hydrogen, ($C_1$-$C_6$)alkyl and $C_{3-7}$ carbocyclyl; and
each $R^{3C}$ is independently selected from the group consisting of heterocycle, and heteroaryl.

9. A compound of formula (II):

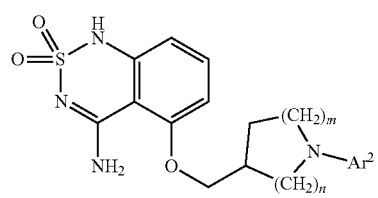

(II)

or a salt thereof, wherein:
$Ar^2$ is an aryl or heteroaryl, each optionally substituted with one or more $R^4$;
each $R^4$ is independently selected from the group consisting of halo, cyano, nitro, oxo, —C(=O)$OR^{4A}$, —$NR^{4A}(CH_2)_mOR^{4B}$, —$NR^{3A}(CH_2)_mR^{4B}$, —$(CH_2)_nOR^{4B}$, —$(CH_2)_nR^{4B}$, —C(=O)$R^{4A}$, halo($C_1$-$C_6$)alkyl, halo($C_1$-$C_6$)alkoxy, ($C_1$-$C_6$)alkylC(=O)—, ($C_1$-$C_6$)alkylOC(=O)—, ($C_1$-$C_6$)alkylC(=O)O—, —C(=O)$NR^{4A}R^{4B}$, —$NR^{4A}$C(=O)$R^{4B}$, and $R^{4C}$;
each $R^{4A}$ is independently selected from the group consisting of hydrogen, halo, cyano, —$(CH_2)_nOH$, —(CH$_2$)$_n$R$^{4AA}$, —(CH$_2$)$_n$OR$^{4AA}$, —(CH$_2$)$_n$N(R$^{4AA}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl, said heterocycle, aryl and heteroaryl in R$^{4A}$, each optionally substituted with one or more (C$_1$-C$_6$)alkyl or C$_{3-7}$ carbocyclyl;

each R$^{4B}$ is independently selected from the group consisting of hydrogen, halo, cyano, —(CH$_2$)$_n$OH, —(CH$_2$)$_n$R$^{4BB}$, —(CH$_2$)$_n$OR$^{4BB}$, —(CH$_2$)$_n$N(R$^{4BB}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;

each R$^{4C}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, heteroaryl(C$_1$-C$_6$)alkyl, and C$_{3-7}$ carbocyclyl, each optionally substituted with one or more R$^{4CC}$;

each R$^{4AA}$ is independently selected from the group consisting of hydrogen, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{4CC}$;

each R$^{4BB}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{4CC}$;

each R$^{4CC}$ is independently selected from the group consisting of halo, cyano, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl;

each m is independently an integer selected from 0, 1, 2, and 3;

each n is independently an integer selected from 0, 1, 2 and 3;

each p is independently an integer selected from 1, 2, and 3; and each q is independently an integer selected from 0, 1, 2 and 3.

10. The compound of Embodiment 9, which is a compound of formula (IIa):

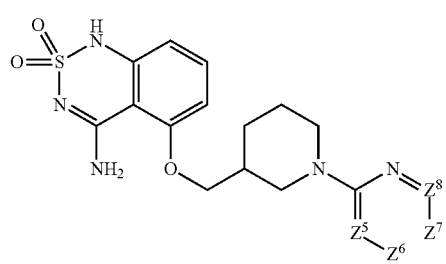

(IIa)

or a salt thereof, wherein:

Z$^5$ is —CH—, —CR$^4$—, or N (nitrogen);
Z$^6$ is —CH— or —CR$^4$—;
Z$^7$ is —CH—, —CR$^4$—, or N (nitrogen); and
Z$^8$ is —CH— or —CR$^4$—.

11. The compound of Embodiment 10, wherein Z$^5$ is —CH—.

12. The compound of Embodiment 10, wherein Z$^5$ is N (nitrogen).

13. The compound of any one of Embodiments 10-12, wherein at least one of Z$^6$, Z$^7$ and Z$^8$ is —CR$^4$—.

14. The compound of Embodiment 13,
wherein:
each R$^4$ is independently selected from the group consisting of halo, —NR$^{4A}$(CH$_2$)$_p$OR$^{4B}$, —NR$^{4A}$(CH$_2$)$_p$R$^{4B}$, —(CH$_2$)$_q$OR$^{4B}$, —(CH$_2$)$_q$R$^{4B}$ and R$^{4C}$;
each R$^{4A}$ is independently selected from the group consisting of hydrogen and (C$_1$-C$_6$)alkyl;
each R$^{4B}$ is independently selected from the group consisting of hydrogen, (C$_1$-C$_6$)alkyl and C$_{3-7}$ carbocyclyl; and
each R$^{4C}$ is independently selected from the group consisting of heterocycle, and heteroaryl.

15. The compound of Embodiment 13,
wherein:
each R$^4$ is independently selected from the group consisting of —C(=O)OR$^{4A}$, —C(=O)NR$^{4A}$R$^{4B}$, and —C(=O)R$^{4A}$;
each R$^{4A}$ is independently selected from the group consisting of hydrogen, —(CH$_2$)$_n$OH, —(CH$_2$)$_n$R$^{4AA}$, —(CH$_2$)$_n$OR$^{4AA}$, —(CH$_2$)$_n$N(R$^{4AA}$)$_2$, aryl, heteroaryl, (C$_1$-C$_6$)alkyl, heterocycle and heterocycle substituted with one or more (C$_1$-C$_6$)alkyl;
each R$^{4B}$ is independently selected from the group consisting of hydrogen, (C$_1$-C$_6$)alkyl and C$_{3-7}$ carbocyclyl; and
each R$^{4C}$ is independently selected from the group consisting of heterocycle, and heteroaryl.

16. The compound of Embodiment 15, wherein each R$^{4AA}$ is independently selected from the group consisting of hydrogen, (C$_1$-C$_6$)alkyl, C$_{3-7}$ carbocyclyl, heterocycle, aryl and heteroaryl.

17. A compound listed in Tables 1, 2, 3, 4, 5 or 6, or a salt thereof.

18. An ingestible composition, comprising the compound of any one of Embodiments 1-17 and, optionally, a sweetener.

19. The composition of Embodiment 0, further comprising a vehicle.

20. The composition of Embodiment 19, wherein the vehicle is water.

21. The composition Embodiment 0, wherein the compound is present at a concentration at or below its sweetness recognition threshold.

22. The composition of Embodiment 0, wherein the sweetener is present in an amount from about 0.1% to about 12% by weight.

23. The composition of Embodiment 0, wherein the sweetener is present in an amount from about 2% to about 8% by weight.

24. The composition of Embodiment 0, wherein the sweetener is a sugar.

25. The composition of Embodiment 24, wherein the sweetener is sucrose.

26. The composition of Embodiment 24, wherein the sweetener comprises a combination of fructose and glucose.

27. The composition of Embodiment 0, wherein the sweetener is sucralose.

28. The composition of Embodiment 0, wherein the composition is a beverage.

29. The composition of Embodiment 28, wherein the beverage is selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies.

30. The composition of Embodiment 28, wherein the beverage is a soft drink.

31. A method of enhancing sweetness of a sweetener, comprising combining the compound of any one of Embodiments 1-17 with the sweetener.

32. The method of Embodiment 31, wherein the sweetener is a sugar.

33. The method of Embodiment 32, wherein the sweetener is sucrose.

34. The composition of Embodiment 32, wherein the sweetener comprises a combination of fructose and glucose.

35. The method of Embodiment 31, wherein the sweetener is sucralose.

36. Use of the compound of any one of Embodiments 1-17.

37. Use of the compound of any one of Embodiments 1-17 to enhance the sweetness of a composition.

38. The use of Embodiment 37, wherein the composition comprises one or more sweeteners.

39. The use of Embodiment 38, wherein the one or more sweeteners comprise sucrose, fructose, sucralose, aspartame, acesulfame K, one or more rebaudiosides, one or more sugar alcohols, one or more mogrosides, or any combinations thereof.

40. The use of Embodiment 38, wherein the one or more sweeteners comprise sucrose.

41. The use of Embodiment 38, wherein the one or more sweeteners comprise fructose.

42. The use of Embodiment 38, wherein the one or more sweeteners comprise sucralose.

43. The use of Embodiment 38, wherein the one or more sweeteners comprise glucose.

What is claimed is:
1. A compound of formula (I):

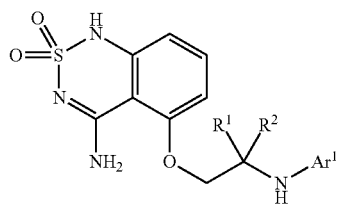

(I)

or a salt thereof, wherein:
$R^1$ and $R^2$ are each independently hydrogen or $C_{1-6}$ alkyl, or $R^1$ and $R^2$ together with the carbon to which they are attached is a $C_{3-7}$ carbocyclyl;
$Ar^1$ is an aryl or heteroaryl, each optionally substituted with one or more $R^3$;

each $R^3$ is independently selected from the group consisting of halo, cyano, nitro, oxo, —C(=O)OR$^{3A}$, —NR$^{3A}$(CH$_2$)$_p$OR$^{3B}$, —NR$^{3A}$(CH$_2$)$_p$R$^{3B}$, (CH$_2$)$_q$OR$^{3B}$, —(CH$_2$)$_q$R$^{3B}$, —C(=O)R$^{3A}$, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, —C(=O)NR$^{3A}$R$^{3B}$, —NR$^{3A}$C(=O)R$^{3B}$, and R$^{3C}$;

each $R^{3A}$ is independently selected from the group consisting of hydrogen, halo, cyano, —(CH$_2$)$_q$R$^{3AA}$, (CH$_2$)$_q$N(R$^{3AA}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;

each $R^{3B}$ is independently selected from the group consisting of hydrogen, halo, cyano, —(CH$_2$)$_q$R$^{3BB}$, —(CH$_2$)$_q$N(R$^{3BB}$)$_2$, (C$_1$-C$_6$)alkyl, C$_{3-7}$ carbocyclyl, (C$_1$-C$_6$)alkoxy, halo(C$_1$-C$_6$)alkyl, halo(C$_1$-C$_6$)alkoxy, (C$_1$-C$_6$)alkylC(=O)—, (C$_1$-C$_6$)alkylOC(=O)—, (C$_1$-C$_6$)alkylC(=O)O—, heterocycle, aryl, heteroaryl, heterocycle(C$_1$-C$_6$)alkyl, aryl(C$_1$-C$_6$)alkyl, and heteroaryl(C$_1$-C$_6$)alkyl;

each $R^{3C}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, heteroaryl(C$_1$-C$_6$)alkyl, and C$_{3-7}$ carbocyclyl, each optionally substituted with one or more R$^{3CC}$;

each $R^{3AA}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{3CC}$;

each $R^{3BB}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{3CC}$;

each $R^{3CC}$ is independently selected from the group consisting of halo, cyano, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl;

each p is independently an integer selected from 1, 2, and 3; and each q is independently an integer selected from 0, 1, 2 and 3.

2. The compound of claim 1, which is a compound of formula (Ia):

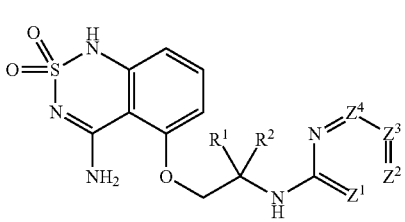

(Ia)

or a salt thereof, wherein:
$Z^1$ is —CH—, —CR$^3$—, or N (nitrogen);
$Z^2$ is —CH— or —CR$^3$—;
$Z^3$ is —CH—, —CR$^3$—, or N (nitrogen); and
$Z^4$ is —CH— or —CR$^3$—.

3. The compound of claim 2, wherein $Z^1$ is N (nitrogen), and $Z^3$ is —CH— or —CR$^3$—.

4. The compound of claim 2, wherein $Z^1$ and $Z^3$ are independently —CH— or —CR$^3$—.

5. The compound of claim 2, wherein $Z^3$ is N (nitrogen), and $Z^1$ is —CH— or —CR$^3$—.

6. The compound of claim 1, wherein:
   each $R^3$ is independently selected from the group consisting of halo, —NR$^{3A}$(CH$_2$)$_p$OR$^{3B}$, —NR$^{3A}$(CH$_2$)$_p$R$^{3B}$, —(CH$_2$)$_q$OR$^{3B}$, —(CH$_2$)$_q$R$^{3B}$ and R$^{3C}$;
   each $R^{3A}$ is independently selected from the group consisting of hydrogen, and (C$_1$-C$_6$)alkyl;
   each $R^{3B}$ is independently selected from the group consisting of hydrogen, (C$_1$-C$_6$)alkyl and C$_{3-7}$ carbocyclyl; and
   each $R^{3C}$ is independently selected from the group consisting of heterocycle, and heteroaryl.

7. A compound of formula (II):

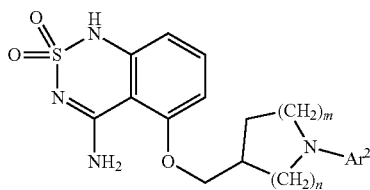

(II)

or a salt thereof, wherein:
   Ar$^2$ is an aryl or heteroaryl, each optionally substituted with one or more R$^4$;
   each $R^4$ is independently selected from the group consisting of halo, cyano, nitro, oxo, —C(=O)OR$^{4A}$, —NR$^{4A}$(CH$_2$)$_m$OR$^{4B}$, —NR$^{4A}$(CH$_2$)$_m$R$^{4B}$, —(CH$_2$)$_n$OR$^{4B}$, —(CH$_2$)$_n$R$^{4B}$, —C(=O)R$^{4A}$, halo(C$_1$-C$_6$)alkyl, halo (C$_1$-C$_6$)alkoxy, (C$_1$-C$_6$)alkylC(=O)—, (C$_1$-C$_6$)alkylOC(=O)—, (C$_1$-C$_6$)alkylC(=O)O—, —C(=O) NR$^{4A}$R$^{4B}$, —NR$^{4A}$C(=O)R$^{4B}$, and R$^{4C}$;
   each $R^{4A}$ is independently selected from the group consisting of hydrogen, halo, cyano, —(CH$_2$)$_n$OH, —(CH$_2$)$_n$R$^{4AA}$, —(CH$_2$)$_n$OR$^{4AA}$, —(CH$_2$)$_n$N(R$^{4AA}$)$_2$, (C$_1$-C$_6$)alkyl, C$_{3-7}$ carbocyclyl, (C$_1$-C$_6$)alkoxy, halo (C$_1$-C$_6$)alkyl, halo(C$_1$-C$_6$)alkoxy, (C$_1$-C$_6$)alkylC (=O)—, (C$_1$-C$_6$)alkylOC(=O)—, (C$_1$-C$_6$)alkylC (=O)O—, heterocycle, aryl, heteroaryl, heterocycle (C$_1$-C$_6$)alkyl, aryl(C$_1$-C$_6$)alkyl, and heteroaryl(C$_1$-C$_6$) alkyl, said heterocycle, aryl and heteroaryl in R$^{4A}$, each optionally substituted with one or more (C$_1$-C$_6$)alkyl or C$_{3-7}$ carbocyclyl;
   each $R^{4B}$ is independently selected from the group consisting of hydrogen, halo, cyano, —(CH$_2$)$_n$OH, —(CH$_2$)$_n$R$^{4BB}$, —(CH$_2$)$_n$OR$^{4BB}$, —(CH$_2$)$_n$N(R$^{4BB}$)$_2$, (C$_1$-C$_6$)alkyl, C$_{3-7}$ carbocyclyl, (C$_1$-C$_6$)alkoxy, halo (C$_1$-C$_6$)alkyl, halo(C$_1$-C$_6$)alkoxy, (C$_1$-C$_6$)alkylC (=O)—, (C$_1$-C$_6$)alkylOC(=O)—, (C$_1$-C$_6$)alkylC (=O)O—, heterocycle, aryl, heteroaryl, heterocycle (C$_1$-C$_6$)alkyl, aryl(C$_1$-C$_6$)alkyl, and heteroaryl(C$_1$-C$_6$) alkyl;
   each $R^{4C}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$) alkyl, heteroaryl(C$_1$-C$_6$)alkyl, and C$_{3-7}$ carbocyclyl, each optionally substituted with one or more R$^{4CC}$;
   each $R^{4AA}$ is independently selected from the group consisting of hydrogen, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl, each optionally substituted with one or more R$^{4CC}$;
   each $R^{4BB}$ is independently selected from the group consisting of (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$) alkyl, and C$_{3-7}$ carbocyclyl, each optionally substituted with one or more R$^{4CC}$;
   each $R^{4CC}$ is independently selected from the group consisting of halo, cyano, (C$_1$-C$_6$)alkyl, (C$_1$-C$_6$)alkoxy, heterocycle, aryl, heteroaryl, heterocycle(C$_1$-C$_6$)alkyl, aryl(C$_1$-C$_6$)alkyl, and C$_{3-7}$ carbocyclyl;
   each m is independently an integer selected from 0, 1, 2, and 3; and
   each n is independently an integer selected from 0, 1, 2 and 3.

8. The compound of claim 7, which is a compound of formula (IIa):

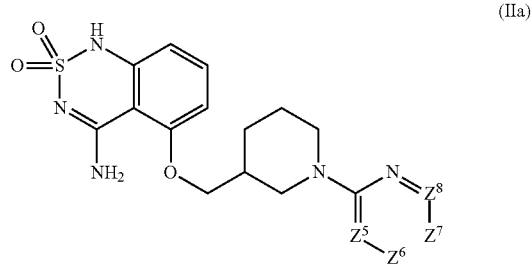

(IIa)

or a salt thereof, wherein:
   $Z^5$ is —CH—, —CR$^4$—, or N (nitrogen);
   $Z^6$ is —CH— or —CR$^4$—;
   $Z^7$ is —CH—, —CR$^4$—, or N (nitrogen); and
   $Z^8$ is —CH— or —CR$^4$—.

9. The compound of claim 8, wherein $Z^5$ is N, and $Z^6$, $Z^7$, and $Z^8$ are independently —CH— or —CR$^4$—.

10. The compound of claim 8, wherein at least one of (or in some cases, one of) $Z^6$, $Z^7$ and $Z^8$ is —CR$^4$—.

11. The compound of claim 8, wherein $Z^5$, $Z^6$, and $Z^7$ are —CH—, and $Z^8$ is —CR$^4$—.

12. The compound of claim 8, wherein $Z^5$, $Z^6$, and $Z^8$ are —CH—, and $Z^7$ is —CR$^4$—.

13. The compound of claim 8, wherein $Z^5$, $Z^7$, and $Z^8$ are —CH—, and $Z^6$ is —CR$^4$—.

14. The compound of claim 7, wherein:
   each $R^4$ is independently selected from the group consisting of halo, —NR$^{4A}$(CH$_2$)$_m$OR$^{4B}$, —NR$^{4A}$(CH$_2$)$_m$R$^{4B}$, —(CH$_2$)$_n$OR$^{4B}$, —(CH$_2$)$_n$R$^{4B}$ and R$^{4C}$;
   each $R^{4A}$ is independently selected from the group consisting of hydrogen and (C$_1$-C$_6$)alkyl;
   each $R^{4B}$ is independently selected from the group consisting of hydrogen, (C$_1$-C$_6$)alkyl and C$_{3-7}$ carbocyclyl; and
   each $R^{4C}$ is independently selected from the group consisting of heterocycle and heteroaryl.

15. An ingestible composition, which comprises: (a) the compound of claim 1; and (b) a sweetener, such as sucrose, fructose, glucose, sucralose, or any combination thereof.

* * * * *

UNITED STATES PATENT AND TRADEMARK OFFICE
CERTIFICATE OF CORRECTION

PATENT NO. : 11,945,813 B2
APPLICATION NO. : 17/266074
DATED : April 2, 2024
INVENTOR(S) : Joseph R. Fotsing et al.

It is certified that error appears in the above-identified patent and that said Letters Patent is hereby corrected as shown below:

In the Claims

Column 84, Line 3, Claim 1, delete "$(CH_2)_qOR^{3B}$," and insert -- —$(CH_2)_qOR^{3B}$, --.

Column 84, Line 10 (approx.), Claim 1, delete "$(CH_2)_qN(R^{3AA})_2$," and insert -- —$(CH_2)_qN(R^{3AA})_2$, --.

Column 86, Line 4, Claim 7, delete "$C_{3—7}$" and insert -- $C_{3-7}$ --.

Signed and Sealed this
Twenty-seventh Day of August, 2024

Katherine Kelly Vidal
*Director of the United States Patent and Trademark Office*